(12) United States Patent
Sims et al.

(10) Patent No.: US 7,261,894 B2
(45) Date of Patent: Aug. 28, 2007

(54) METHODS OF TREATING INFLAMMATORY AND/OR AUTOIMMUNE DISEASE

(75) Inventors: John E Sims, Seattle, WA (US); Dirk E Smith, Bainbridge Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 286 days.

(21) Appl. No.: 10/991,812

(22) Filed: Nov. 18, 2004

(65) Prior Publication Data

US 2005/0208051 A1 Sep. 22, 2005

Related U.S. Application Data

(60) Division of application No. 09/970,033, filed on Oct. 2, 2001, now Pat. No. 6,838,290, which is a continuation-in-part of application No. 09/763,498, filed on Aug. 20, 1999, now Pat. No. 6,949,359, and a continuation-in-part of application No. PCT/US99/18771, filed on Aug. 20, 1999.

(60) Provisional application No. 60/313,110, filed on Aug. 16, 2001, provisional application No. 60/099,974, filed on Sep. 11, 1998, provisional application No. 60/098,595, filed on Aug. 31, 1998, provisional application No. 60/097,413, filed on Aug. 21, 1998.

(51) Int. Cl.
*A61K 39/395* (2006.01)
*A61K 39/00* (2006.01)

(52) U.S. Cl. ............... 424/145.1; 424/184.1; 424/185.2; 424/85.2; 514/12

(58) Field of Classification Search ............ None
See application file for complete search history.

(56) References Cited

U.S. PATENT DOCUMENTS 5,449,758 A 9/1995 Hartley .......... 530/350

6,197,551 B1 3/2001 Busfield .......... 435/70.1

FOREIGN PATENT DOCUMENTS

| EP | 0 855 404 A | 7/1998 |
|----|-------------|--------|
| WO | WO 98/47921 | 10/1998 |
| WO | WO98/47921 | 10/1998 |
| WO | WO 99/37662 | 7/1999 |
| WO | WO99/37662 | 7/1999 |

OTHER PUBLICATIONS

Database EMBL. Entry MMA30324, Accession No. AA030324, Jan. 21, 1997, 2125184, Marra et al.
Dinarello, C.A., "Interleukin-1," *Cytokine and Growth Factor Review* vol. 8(4):253-265.
Bowie J.U. et al., "Deciphering the message in protein sequence tolerance to amino acid substitutions," *Science* 247:1306-1310, 1990.
Geysen H.M. et al., "Cognitive features of continuous antigenic determinants," *J Mol Recognit* 1:32-41, 1988.
Colman P.M., "Effects of amino acid sequence changes on antibody-antigen interactions," *Research in Immunology* 145:33-36, 1994.
Dinarello, C.A., "Interleukin-1," *Cytokine and Growth Factor Review* vol. 8(4):253-265, 1997.

*Primary Examiner*—Eileen O'Hara
*Assistant Examiner*—Fozia Hamud
(74) *Attorney, Agent, or Firm*—Patricia Anne Perkins

(57) ABSTRACT

The invention is directed to purified and isolated novel human IL-1 epsilon polypeptides, the nucleic acids encoding such polypeptides, processes for production of recombinant forms of such polypeptides, antibodies generated against these polypeptides, the use of such polypeptides in cellular and immune reactions, the use of such polypeptides in screening for agonists or antagonists of IL-1 epsilon activity, and kits comprising such polypeptides.

6 Claims, 4 Drawing Sheets

NAME: Human IL-1 epsilon DNA

Nucleotide sequence:

GAAAAGGATA TAATGGATTT GTACAACCAA CCCGAGCCTG TGAAGTCCTT
TCTCTTCTAC CACAGCCAGA GTGGCAGGAA CTCCACCTTC GAGTCTGTGG
CTTTCCCTGG CTGGTTCATC GCTGTCAGCT CTGAAGGAGG CTGTCCTCTC
ATCCTTACCC AAGAACTGGG GAAAGCCAAC ACTACTGACT TTGGGTTAAC
TATGCTGTTT TAA
(SEQ ID NO:5)

ATGGAAAAAG CATTGAAAAT TGACACACCT CAGCAGGGGA GCATTCAGGA
TATCAATCAT CGGGTGTGGG TTCTTCAGGA CCAGACGCTC ATAGCAGTCC
CGAGGAAGGA CCGTATGTCT CCAGTCACTA TTGCCTTAAT CTCATGCCGA
CATGTGGAGA CCCTTGAGAA AGACAGAGGG AACCCCATCT ACCTGGGCCT
GAATGGACTC AATCTCTGCC TGATGTGTGC TAAAGTCGGG GACCAGCCCA
CACTGCAGCT GAAGGAAAAG GATATAATGG ATTTGTACAA CCAACCCGAG
CCTGTGAAGT CCTTTCTCTT CTACCACAGC CAGAGTGGCA GGAACTCCAC
CTTCGAGTCT GTGGCTTTCC CTGGCTGGTT CATCGCTGTC AGCTCTGAAG
GAGGCTGTCC TCTCATCCTT ACCCAAGAAC TGGGGAAAGC CAACACTACT
GACTTTGGGT TAACTATGCT GTTTTAA
(SEQ ID NO:7)

ATGGAAAAAG CATTGAAAAT TGACACACCT CAGCGGGGGA GCATTCAGGA
TATCAATCAT CGGGTGTGGG TTCTTCAGGA CCAGACGCTC ATAGCAGTCC
CGAGGAAGGA CCGTATGTCT CCAGTCACTA TTGCCTTAAT CTCATGCCGA
CATGTGGAGA CCCTTGAGAA AGACAGAGGG AACCCCATCT ACCTGGGCCT
GAATGGACTC AATCTCTGCC TGATGTGTGC TAAAGTCGGG GACCAGCCCA
CACTGCAGCT GAAGGAAAAG GATATAATGG ATTTGTACAA CCAACCCGAG
CCTGTGAAGT CCTTTCTCTT CTACCACAGC CAGAGTGGCA GGAACTCCAC
CTTCGAGTCT GTGGCTTTCC CTGGCTGGTT CATCGCTGTC AGCTCTGAAG
GAGGCTGTCC TCTCATCCTT ACCCAAGAAC TGGGGAAAGC CAACACTACT
GACTTTGGGT TAACTATGCT GTTTTAA
(SEQ ID NO:12)

FIGURE 1

NAME: Human IL-1 epsilon polypeptide

Translation in relevant reading frame (5' 3'):

EKDIMDLYNQ PEPVKSFLFY HSQSGRNSTF ESVAFPGWFI AVSSEGGCPL
ILTQELGKAN TTDFGLTMLF *
(SEQ ID NO:6)

MEKALKIDTP QQGSIQDINH RVWVLQDQTL IAVPRKDRMS PVTIALISCR
HVETLEKDRG NPIYLGLNGL NLCLMCAKVG DQPTLQLKEK DIMDLYNQPE
PVKSFLFYHS QSGRNSTFES VAFPGWFIAV SSEGGCPLIL TQELGKANTT
DFGLTMLF*
(SEQ ID NO:8)

MEKALKIDTP QRGSIQDINH RVWVLQDQTL IAVPRKDRMS PVTIALISCR
HVETLEKDRG NPIYLGLNGL NLCLMCAKVG DQPTLQLKEK DIMDLYNQPE
PVKSFLFYHS QSGRNSTFES VAFPGWFIAV SSEGGCPLIL TQELGKANTT
DFGLTMLF*
(SEQ ID NO:13)

FIGURE 2 human IL-1 epsilon 3' exon (top) vs. mouse IL-1 epsilon (long form) (bottom):
(64% percent identity)

```
 1 EKDIMDLYNQPEPVKSFLFYHSQSGRNSTFESVAFPGWFIAVSSEGGCPL  50
    ||.|:||. |||.||||||.  ||||||||||.||||||| ||||
29 EGNIMEMYNKKEPVKASLFYHKKSGTTSTFESAAFPGWFIAVCSKGSCPL  78

51 ILTQELGKANTTDFGLTML  69    (SEQ ID NO: 10)
   ||||||| .: ||  |||
79 ILTQELGEIFITDFEMIVV  97    (SEQ ID NO: 11)
```

FIGURE 3

Human IL-1 epsilon (amino acids 51-159) (top)
vs.
Mouse IL-1 epsilon (Long Form) (bottom):

```
 51 HVETLEKDRGNPIYLGLNGLNLCLMCAKVGDQ.PTLQLKEKDIMDLYNQP  99
       : .      |  . .  | . | .| .||::||.
  1 ..........MFRILVVVCGSCRTISSLQSQGKSKQFQEGNIMEMYNKK  39

100 EPVKSFLFYHSQSGRNSTFESVAFPGWFIAVSSEGGCPLILTQELGKANT 149
    ||||. ||||  .||   |||||  |||||||||  |.| |||||||||.
 40 EPVKASLFYHKKSGTTSTFESAAFPGWFIAVCSKGSCPLILTQELGEIFI  89

150 TDFGLTMLF* 159       (SEQ ID NO:9)
    ||| :  .. |
 90 TDFEMIVVH*  99       (SEQ ID NO:2)
```

(53% similarity, 49% identity)

FIGURE 4

SEQUENCE LISTING

<160> NUMBER OF SEQ ID NOS: 13

<210> SEQ ID NO 1
<211> LENGTH: 297
<212> TYPE: DNA
<213> ORGANISM: Mus sp.

<400> SEQUENCE: 1

```
atgttcagga tcttagtagt cgtgtgtgga tcctgcagaa caatatcctc actgcagtcc      60
caaggaaaga gcaaacagtt ccaggaaggg aacataatgg aaatgtacaa caaaaaggaa     120
cctgtaaaag cctctctctt ctatcacaag aagagtggta caacctctac atttgagtct     180
gcagccttcc ctggttggtt catcgctgtc tgctctaaag ggagctgccc actcattctg     240
acccaagaac tgggggaaat cttcatcact gacttcgaga tgattgtggt acattaa       297
```

<210> SEQ ID NO 2
<211> LENGTH: 98
<212> TYPE: PRT
<213> ORGANISM: Mus sp.

<400> SEQUENCE: 2

Met Phe Arg Ile Leu Val Val Val Cys Gly Ser Cys Arg Thr Ile Ser
1               5                   10                  15

Ser Leu Gln Ser Gln Gly Lys Ser Lys Gln Phe Gln Glu Gly Asn Ile
            20                  25                  30

Met Glu Met Tyr Asn Lys Lys Glu Pro Val Lys Ala Ser Leu Phe Tyr
        35                  40                  45

His Lys Lys Ser Gly Thr Thr Ser Thr Phe Glu Ser Ala Ala Phe Pro
    50                  55                  60

Gly Trp Phe Ile Ala Val Cys Ser Lys Gly Ser Cys Pro Leu Ile Leu
65                  70                  75                  80

Thr Gln Glu Leu Gly Glu Ile Phe Ile Thr Asp Phe Glu Met Ile Val
                85                  90                  95

Val His

<210> SEQ ID NO 3
<211> LENGTH: 174
<212> TYPE: DNA
<213> ORGANISM: Mus sp.

<400> SEQUENCE: 3

```
atgttcagga tcttagtagt cgtgtgtgga tcctgcagaa caatatcctc actgcagtcc      60
caaggaaaga gcaaacagtt ccagtcacta ttaccttgct cccatgccaa tatctggaca    120
ctcttgagac gaacaggggg gatcccacgt acatgggagt gcaaaggccg atga          174
```

<210> SEQ ID NO 4
<211> LENGTH: 56
<212> TYPE: PRT

<213> ORGANISM: Mus sp.

<400> SEQUENCE: 4

```
Met Phe Arg Ile Leu Val Val Cys Gly Ser Cys Arg Thr Ile Ser
1               5                   10                  15

Leu Gln Ser Gln Gly Lys Ser Lys Gln Phe Gln Ser Leu Leu Pro Cys
            20                  25                  30

Ser His Ala Asn Ile Trp Thr Leu Leu Arg Arg Thr Gly Gly Ile Pro
            35                  40                  45

Arg Thr Trp Glu Cys Lys Gly Arg
    50                  55
```

<210> SEQ ID NO 5
<211> LENGTH: 213
<212> TYPE: DNA
<213> ORGANISM: Homo sapiens

<400> SEQUENCE: 5

```
gaaaaggata taatggattt gtacaaccaa cccgagcctg tgaagtcctt tctcttctac      60
cacagccaga gtggcaggaa ctccaccttc gagtctgtgg cttttccctgg ctggttcatc    120
gctgtcagct ctgaaggagg ctgtcctctc atccttaccc aagaactggg aaagccaac     180
actactgact ttgggttaac tatgctgttt taa                                  213
```

<210> SEQ ID NO 6
<211> LENGTH: 70
<212> TYPE: PRT
<213> ORGANISM: Homo sapiens

<400> SEQUENCE: 6

```
Glu Lys Asp Ile Met Asp Leu Tyr Asn Gln Pro Glu Pro Val Lys Ser
1               5                   10                  15

Phe Leu Phe Tyr His Ser Gln Ser Gly Arg Asn Ser Thr Phe Glu Ser
            20                  25                  30

Val Ala Phe Pro Gly Trp Phe Ile Ala Val Ser Ser Glu Gly Gly Cys
            35                  40                  45

Pro Leu Ile Leu Thr Gln Glu Leu Gly Lys Ala Asn Thr Thr Asp Phe
    50                  55                  60

Gly Leu Thr Met Leu Phe
65                  70
```

<210> SEQ ID NO 7
<211> LENGTH: 477
<212> TYPE: DNA
<213> ORGANISM: Homo sapiens

<400> SEQUENCE: 7

```
atggaaaaag cattgaaaat tgacacacct cagcagggga gcattcagga tatcaatcat      60
cgggtgtggg ttcttcagga ccagacgctc atagcagtcc gaggaaggga ccgtatgtct    120
ccagtcacta ttgccttaat ctcatgccga catgtggaga cccttgagaa agacagaggg    180
aaccccatct acctgggcct gaatggactc aatctctgcc tgatgtgtgc taaagtcggg    240
gaccagccca cactgcagct gaaggaaaag gatataatgg atttgtacaa ccaacccgag    300
cctgtgaagt cctttctctt ctaccacagc cagagtggca ggaactccac cttcgagtct    360
gtggctttcc ctggctggtt catcgctgtc agctctgaag gaggctgtcc tctcatcctt    420
acccaagaac tggggaaagc caacactact gactttgggt taactatgct gttttaa      477
```

```
<210> SEQ ID NO 8
<211> LENGTH: 158
<212> TYPE: PRT
<213> ORGANISM: Homo sapiens

<400> SEQUENCE: 8

Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
            20                  25                  30

Val Pro Arg Lys Asp Arg Met Ser Pro Val Thr Ile Ala Leu Ile Ser
        35                  40                  45

Cys Arg His Val Glu Thr Leu Glu Lys Asp Arg Gly Asn Pro Ile Tyr
    50                  55                  60

Leu Gly Leu Asn Gly Leu Asn Leu Cys Leu Met Cys Ala Lys Val Gly
65                  70                  75                  80

Asp Gln Pro Thr Leu Gln Leu Lys Glu Lys Asp Ile Met Asp Leu Tyr
                85                  90                  95

Asn Gln Pro Glu Pro Val Lys Ser Phe Leu Phe Tyr His Ser Gln Ser
            100                 105                 110

Gly Arg Asn Ser Thr Phe Glu Ser Val Ala Phe Pro Gly Trp Phe Ile
        115                 120                 125

Ala Val Ser Ser Glu Gly Gly Cys Pro Leu Ile Leu Thr Gln Glu Leu
    130                 135                 140

Gly Lys Ala Asn Thr Thr Asp Phe Gly Leu Thr Met Leu Phe
145                 150                 155

<210> SEQ ID NO 9
<211> LENGTH: 108
<212> TYPE: PRT
<213> ORGANISM: Homo sapiens

<400> SEQUENCE: 9

His Val Glu Thr Leu Glu Lys Asp Arg Gly Asn Pro Ile Tyr Leu Gly
1               5                   10                  15

Leu Asn Gly Leu Asn Leu Cys Leu Met Cys Ala Lys Val Gly Asp Gln
            20                  25                  30

Pro Thr Leu Gln Leu Lys Glu Lys Asp Ile Met Asp Leu Tyr Asn Gln
        35                  40                  45

Pro Glu Pro Val Lys Ser Phe Leu Phe Tyr His Ser Gln Ser Gly Arg
    50                  55                  60

Asn Ser Thr Phe Glu Ser Val Ala Phe Pro Gly Trp Phe Ile Ala Val
65                  70                  75                  80

Ser Ser Glu Gly Gly Cys Pro Leu Ile Leu Thr Gln Glu Leu Gly Lys
                85                  90                  95

Ala Asn Thr Thr Asp Phe Gly Leu Thr Met Leu Phe
            100                 105

<210> SEQ ID NO 10
<211> LENGTH: 69
<212> TYPE: PRT
<213> ORGANISM: Homo sapiens

<400> SEQUENCE: 10

Glu Lys Asp Ile Met Asp Leu Tyr Asn Gln Pro Glu Pro Val Lys Ser
1               5                   10                  15

Phe Leu Phe Tyr His Ser Gln Ser Gly Arg Asn Ser Thr Phe Glu Ser
```

```
              20                  25                  30
Val Ala Phe Pro Gly Trp Phe Ile Ala Val Ser Ser Glu Gly Gly Cys
         35                  40                  45

Pro Leu Ile Leu Thr Gln Glu Leu Gly Lys Ala Asn Thr Thr Asp Phe
     50                  55                  60

Gly Leu Thr Met Leu
 65

<210> SEQ ID NO 11
<211> LENGTH: 77
<212> TYPE: PRT
<213> ORGANISM: Mus sp.

<400> SEQUENCE: 11

Gln Gly Lys Ser Lys Gln Phe Gln Glu Gly Asn Ile Met Glu Met Tyr
 1               5                  10                  15

Asn Lys Lys Glu Pro Val Lys Ala Ser Leu Phe Tyr His Lys Lys Ser
             20                  25                  30

Gly Thr Thr Ser Thr Phe Glu Ser Ala Ala Phe Pro Gly Trp Phe Ile
         35                  40                  45

Ala Val Cys Ser Lys Gly Ser Cys Pro Leu Ile Leu Thr Gln Glu Leu
     50                  55                  60

Gly Glu Ile Phe Ile Thr Asp Phe Glu Met Ile Val Val
 65                  70                  75

<210> SEQ ID NO 12
<211> LENGTH: 477
<212> TYPE: DNA
<213> ORGANISM: Homo sapiens

<400> SEQUENCE: 12
atggaaaaag cattgaaaat tgacacacct cagcggggga gcattcagga tatcaatcat      60
cgggtgtggg ttcttcagga ccagacgctc atagcagtcc gaggaaggga ccgtatgtct     120
ccagtcacta ttgccttaat ctcatgccga catgtggaga cccttgagaa agacagaggg     180
aaccccatct acctgggcct gaatggactc aatctctgcc tgatgtgtgc taaagtcggg     240
gaccagccca cactgcagct gaaggaaaag gatataatgg atttgtacaa ccaacccgag     300
cctgtgaagt cctttctctt ctaccacagc cagagtggca ggaactccac cttcgagtct     360
gtggctttcc ctggctggtt catcgctgtc agctctgaag gaggctgtcc tctcatcctt     420
acccaagaac tggggaaagc caacactact gactttgggt taactatgct gttttaa       477

<210> SEQ ID NO 13
<211> LENGTH: 158
<212> TYPE: PRT
<213> ORGANISM: Homo sapiens

<400> SEQUENCE: 13

Met Glu Lys Ala Leu Lys Ile Asp Thr Pro Gln Arg Gly Ser Ile Gln
 1               5                  10                  15

Asp Ile Asn His Arg Val Trp Val Leu Gln Asp Gln Thr Leu Ile Ala
             20                  25                  30

Val Pro Arg Lys Asp Arg Met Ser Pro Val Thr Ile Ala Leu Ile Ser
         35                  40                  45

Cys Arg His Val Glu Thr Leu Glu Lys Asp Arg Gly Asn Pro Ile Tyr
     50                  55                  60

Leu Gly Leu Asn Gly Leu Asn Leu Cys Leu Met Cys Ala Lys Val Gly
```

-continued

```
            65                  70                  75                  80
Asp Gln Pro Thr Leu Gln Leu Lys Glu Lys Asp Ile Met Asp Leu Tyr
                85                  90                  95

Asn Gln Pro Glu Pro Val Lys Ser Phe Leu Phe Tyr His Ser Gln Ser
            100                 105                 110

Gly Arg Asn Ser Thr Phe Glu Ser Val Ala Phe Pro Gly Trp Phe Ile
        115                 120                 125

Ala Val Ser Ser Glu Gly Gly Cys Pro Leu Ile Leu Thr Gln Glu Leu
            130                 135                 140

Gly Lys Ala Asn Thr Thr Asp Phe Gly Leu Thr Met Leu Phe
145                 150                 155
```

METHODS OF TREATING INFLAMMATORY AND/OR AUTOIMMUNE DISEASE

CROSS-REFERENCE TO RELATED APPLICATIONS

This application is a divisional of Ser. No. 09/970,033 filed Oct. 2, 2001, now U.S. Pat. No. 6,838,290, which is a continuation-in-part of U.S. application Ser. No. 09/763,498 filed Aug. 20, 1999, now U.S. Pat. No. 6,949,359, and International application No. PCT/US99/18771 filed Aug. 20, 1999, and claims the benefit of U.S. Provisional application Nos. 60/097,413, 60/098,595, 60/099,974, and 60/313,110 filed Aug. 21, 1998, Aug. 31, 1998, Sep. 11, 1998, and Aug. 16, 2001, respectively. The entire disclosures of these applications are relied upon and incorporated by reference herein.

BACKGROUND OF THE INVENTION

1. Field of the Invention

The invention is directed to purified and isolated novel human IL-1 epsilon polypeptides, the nucleic acids encoding such polypeptides, processes for production of recombinant forms of such polypeptides, antibodies generated against these polypeptides, the use of such polypeptides in cellular and immune reactions, the use of such polypeptides in screening for agonists or antagonists of IL-1 epsilon activity, and kits comprising such polypeptides.

2. Description of Related Art

Interleukin-1 (IL-1) is a member of a large group of cytokines whose primary function is to mediate immune and inflammatory responses. There are five known IL-1 family members which include IL-1 alpha, IL-1 beta, IL-1 receptor antagonist (IL-1), IL-1 delta (as disclosed in PCT US/99/00514), and IL-18 (previously known as IGIF and sometimes IL-1 gamma). IL-1 that is secreted by macrophages is actually a mixture of mostly IL-1 beta and some IL-1 alpha (Abbas et al., 1994). IL-1 alpha and IL-1 beta, which are first produced as 33 kD precursors that lack a signal sequence, are further processed by proteolytic cleavage to produce secreted active forms, each about 17 kD. Additionally, the 33 kD precursor of IL-1 alpha is also active. Both forms of IL-1 are the products of two different genes located on chromosome 2. Although the two forms are less than 30 percent homologous to each other, they both bind to the same receptors and have similar activities.

IL-1ra, a biologically inactive form of IL-1, is structurally homologous to IL-1 and binds to the same receptors. Additionally, IL-1ra is produced with a signal sequence which allows for efficient secretion into the extracellular region where it competitively competes with IL-1 (Abbas et al., 1994).

The IL-1 family ligands bind to two IL-1 receptors that are members of the Ig superfamily. IL-1 receptors include the 80 kDa type I receptor (IL-1RI) and a 68 kDa type II receptor (IL-1RII). The ligands also bind to a soluble proteolytic fragment of IL-1RII (sIL-1RII) (Colotta et al., *Science* 261 (5120):472-75, 1993).

The major source of IL-1 is the activated macrophage or mononuclear phagocyte. Other cells that produce IL-1 include epithelial and endothelial cells (Abbas et al., 1994). IL-1 secretion from macrophages occurs after the macrophage encounters and ingests gram-negative bacteria. Such bacteria contain lipopolysaccharide (LPS) molecules, also known as endotoxin, in the bacterial cell wall. LPS molecules are the active components that stimulate macrophages to produce tumor necrosis factor (TNF) and IL-1. In this case, IL-1 is produced in response to LPS and TNF production. At low concentrations, LPS stimulates macrophages and activates B-cells and other host responses needed to eliminate the bacterial infection; however, at high concentrations, LPS can cause severe tissue damage, shock, and even death.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. It is also known that IL-1 does not cause hemorrhagic necrosis of tumors or suppress bone marrow stem cell division. Nevertheless, IL-1 is lethal to humans at high concentrations.

Given the important function of IL-1, there is a need in the art for additional members of the IL-1 ligand family. In addition, in view of the continuing interest in protein research and the immune system, the discovery, identification, and roles of new proteins, such as human IL-1 epsilon and its receptors, are at the forefront of modern molecular biology and biochemistry. Despite the growing body of knowledge, there is still a need in the art for the identity and function of proteins involved in cellular and immune responses.

SUMMARY OF THE INVENTION

The invention aids in fulfilling these needs in the art by providing isolated human IL-1 epsilon nucleic acids and polypeptides encoded by these nucleic acids. Specifically, the invention encompasses an isolated human IL-1 epsilon nucleic acid molecule comprising the DNA sequences of SEQ ID NO:5, SEQ ID NO:7, and SEQ ID NO:12 and an isolated human IL-1 epsilon nucleic acid molecule encoding the amino acid sequence of SEQ ID NO:6, SEQ ID NO:8, and SEQ ID NO:13, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA relating to SEQ ID NO:5, SEQ ID NO:7, or SEQ ID NO:12. Also encompassed are isolated nucleic acid molecules that are derived by in vitro mutagenesis from SEQ ID NO:5, SEQ ID NO:7, or SEQ ID NO:12, are degenerate from SEQ ID NO:5, SEQ ID NO:7, or SEQ ID NO:12, are allelic variants of human DNA of the invention, and are species homologs of DNA of the invention. The invention also encompasses recombinant vectors that direct the expression of these nucleic acid molecules and host cells transformed or transfected with these vectors. In addition, the invention encompasses methods of using the nucleic acid noted above in assays to identify chromosomes, map human genes, and study the immune system.

The invention also encompasses isolated polypeptides encoded by these nucleic acid molecules, synthetic polypeptides encoded by these nucleic acid molecules, and peptides and fragments of these polypeptides. Isolated polyclonal or monoclonal antibodies that bind to these polypeptides are also encompassed by the invention. The invention further encompasses methods for the production of IL-1 epsilon polypeptides, including culturing a host cell under conditions promoting expression and recovering the polypeptide from the culture medium. Especially, the expression of IL-1 epsilon polypeptides in bacteria, yeast, plant, insect, and animal cells is encompassed by the invention.

In general, the polypeptides of the invention can be used to study cellular processes such as immune regulation, cell proliferation, cell death, and inflammatory responses. In addition, the IL-1 epsilon ligand polypeptides of the invention (including fragments of IL-1 epsilon), can be used to identify proteins associated with IL-1-like ligands and IL-1-like receptors.

In addition, assays utilizing IL-1 epsilon ligand polypeptides of the invention (including fragments of IL-1 epsilon) to screen for potential inhibitors and/or agonists of activity associated with polypeptide counter-structure molecules, and methods of using the inventive IL-1 epsilon ligand polypeptides as therapeutic agents for the treatment of diseases mediated by IL-1 epsilon ligand polypeptide counter-structure molecules are encompassed by the invention. Further, methods of using IL-1 epsilon ligand polypeptides of the invention in the design of inhibitors and/or agonists thereof are also an aspect of the invention.

Further encompassed by this invention are kits to aid in these determinations.

BRIEF DESCRIPTION OF THE DRAWINGS

This invention will be more fully described with reference to the drawings in which:

FIG. 1 is the nucleotide sequences of human IL-1 epsilon DNA of the invention, SEQ ID NO:5, SEQ ID NO:7, and SEQ ID NO:12.

FIG. 2 is the amino acid sequence of polypeptides, SEQ ID NO:6, SEQ ID NO:8, and SEQ ID NO:13, encoded by the nucleotide sequences of SEQ ID NO:5, SEQ ID NO:7, and SEQ ID NO:12, respectively.

FIG. 3 depicts the amino acid homology between the 3' exon of human IL-1 epsilon and murine IL-1 epsilon (long form).

FIG. 4 depicts the amino acid homology between human IL-1 epsilon (amino acids 51-159) and murine IL-1 epsilon (long form).

DETAILED DESCRIPTION OF THE INVENTION

Interleukin-1 (IL-1) receptors are members of the large Ig superfamily of cytokine receptors, many of which mediate the response of immune system cells, in particular lymphocytes. In recent years, members of the family of ligands that bind to these receptors have been discovered at an accelerated pace. The increase in the number of known IL-1 ligands has been largely due to the advent of gene cloning and sequencing techniques. Amino acid sequences deduced from nucleotide sequences are considered to represent IL-1 ligands if they share homology with other known IL-1 ligands.

Mouse IL-1 epsilon is a homolog of the known IL-1 genes, IL-1 alpha, IL-1 beta, IL-1delta (disclosed in PCT US/99/00514) and IL-1ra, and more recently, IL-18, previously known sometimes as IL-1 gamma. Mouse IL-1 epsilon was first identified by searching the EST database, and discovering an EST corresponding to mouse IL-1 epsilon (accession number AA030324). The entire open reading frame for the "long form" (see below) is contained in this EST.

Mouse IL-1 Epsilon (Long Form) DNA Sequence

```
                                              (SEQ ID NO:1)
ATGTTCAGGA TCTTAGTAGT CGTGTGTGGA TCCTGCAGAA

CAATATCCTC ACTGCAGTCC CAAGGAAAGA GCAAACAGTT

CCAGGAAGGG AACATAATGG AAATGTACAA CAAAAAGGAA

CCTGTAAAAG CCTCTCTCTT CTATCACAAG AAGAGTGGTA

CAACCTCTAC ATTTGAGTCT GCAGCCTTCC CTGGTTGGTT

CATCGCTGTC TGCTCTAAAG GGAGCTGCCC ACTCATTCTG

ACCCAAGAAC TGGGGGAAAT CTTCATCACT GACTTCGAGA

TGATTGTGGT ACATTAA
```

Mouse IL-1 Epsilon (Long Form) Amino Acid Sequence

```
                                              (SEQ ID NO:2)
MFRILVVVCG SCRTISSLQS QGKSKQFQEG NIMEMYNKKE

PVKASLFYHK KSGTTSTFES AAFPGWFIAV CSKGSCPLIL

TQELGEIFIT DFEMIVVH*
```

While showing homology to the IL-1 genes, mouse IL-1 epsilon is unusual in that the EST originally identified appeared to encode the C-terminal two-thirds of an IL-1-like molecule. In addition, during studies of the expression of IL-1 epsilon, it became apparent that there are two, alternatively spliced, forms of mRNA that encode proteins with identical N-termini but divergent C-termini. The longer of these two proteins was that encoded by the original EST. The shorter (sometimes called the "isoform") is approximately one-third the length of a typical IL-1 family molecule.

Mouse IL-1 Epsilon (Short Form) DNA Sequence

```
                                              (SEQ ID NO:3)
ATGTTCAGGA TCTTAGTAGT CGTGTGTGGA TCCTGCAGAA

CAATATCCTC ACTGCAGTCC CAAGGAAAGA GCAAACAGTT

CCAGTCACTA TTACCTTGCT CCCATGCCAA TATCTGGACA

CTCTTGAGAC GAACAGGGGG GATCCCACGT ACATGGGAGT

GCAAAGGCCG ATGA
```

Mouse IL-1 Epsilon (Short Form) Amino Acid Sequence

```
                                              (SEQ ID NO:4)
MFRILVVVCG SCRTISSLQS QGKSKQFQSL LPCSHANIWT

LLRRTGGIPR TWECKGR*
```

These two proteins (the long and the short form), encoded by alternatively spliced versions of the same original RNA transcript, may associate non-covalently and thus form a "whole" IL-1-like molecule.

In any event, using as a probe the mixed cDNAs for mouse long-form and short-form IL-1 epsilon, human IL-1 epsilon has been identified by screening of a human genomic library. Sequencing of a clone obtained from the human genomic library reveals a stretch of DNA which contains an open reading frame, encoding a portion of a protein with high homology to mouse IL-1 epsilon in the same region. The open reading frame appears to be an exon (the 3' most exon of the coding region). The splice acceptor site at the 5' end of this exon is in the identical position to the splice acceptor site of the corresponding exon in mouse IL-1 epsilon.

The DNA and amino acid sequences of this exon corresponding to human IL-1 epsilon are set forth in SEQ ID NO:5 and SEQ ID NO:6, respectively.

Nucleotide Sequence of Human IL-1 Epsilon DNA:

```
                                               (SEQ ID NO:5)
GAAAAGGATA TAATGGATTT GTACAACCAA CCCGAGCCTG

TGAAGTCCTT TCTCTTCTAC CACAGCCAGA GTGGCAGGAA

CTCCACCTTC GAGTCTGTGG CTTTCCCTGG CTGGTTCATC

GCTGTCAGCT CTGAAGGAGG CTGTCCTCTC ATCCTTACCC

AAGAACTGGG GAAAGCCAAC ACTACTGACT TTGGGTTAAC

TATGCTGTTT TAA
```

A preferred polypeptide encoded by the nucleic acid sequence is set forth below:

Amino Acid Sequence of Human IL-1 Epsilon:

Translation in Relevant Reading Frame (5' 3'):

```
                                    (SEQ ID NO:6)
EKDIMDLYNQ PEPVKSFLFY HSQSGRNSTF ESVAFPGWFI

AVSSEGGCPL ILTQELGKAN TTDFGLTMLF*
```

The full-length human IL-1 epsilon DNA sequence was isolated as described in Example I. The DNA and amino acid sequence of the full-length human IL-1 epsilon are set forth in SEQ ID NO:7 and SEQ ID NO:8, respectively.

Full-Length Nucleotide Sequence of Human IL-1 Epsilon DNA:

```
                                               (SEQ ID NO:7)
ATGGAAAAAG CATTGAAAAT TGACACACCT CAGCAGGGGA

GCATTCAGGA TATCAATCAT CGGGTGTGGG TTCTTCAGGA

CCAGACGCTC ATAGCAGTCC CGAGGAAGGA CCGTATGTCT

CCAGTCACTA TTGCCTTAAT CTCATGCCGA CATGTGGAGA

CCCTTGAGAA AGACAGAGGG AACCCCATCT ACCTGGGCCT

GAATGGACTC AATCTCTGCC TGATGTGTGC TAAAGTCGGG

GACCAGCCCA CACTGCAGCT GAAGGAAAAG GATATAATGG

ATTTGTACAA CCAACCCGAG CCTGTGAAGT CCTTTCTCTT

CTACCACAGC CAGAGTGGCA GGAACTCCAC CTTCGAGTCT

GTGGCTTTCC CTGGCTGGTT CATCGCTGTC AGCTCTGAAG

GAGGCTGTCC TCTCATCCTT ACCCAAGAAC TGGGGAAAGC

CAACACTACT GACTTTGGGT TAACTATGCT GTTTTAA
```

Full-Length Amino Acid Sequence of Human IL-1 Epsilon:

Translation in Relevant Reading Frame (5' to 3'):

```
                                           (SEQ ID NO:8)
MEKALKIDTP QQGSIQDINH RVWVLQDQTL IAVPRKDRMS

PVTIALISCR HVETLEKDRG NPIYLGLNGL NLCLMCAKVG

DQPTLQLKEK DIMDLYNQPE PVKSFLFYHS QSGRNSTFES

VAFPGWFIAV SSEGGCPLIL TQELGKANTT DFGLTMLF*
```

In addition, a single nucleotide polymorphism was identified in the human IL-1 epsilon gene. Specifically, the polymorphism comprises an adenosine to guanosine substitution at nucleotide 35. The polypeptide encoded by this polymorphic IL-1 epsilon gene has an arginine residue at position 12 rather than a glutamine residue. The DNA sequence of the human IL-1 epsilon gene containing this single nucleotide polymorphism is set forth in SEQ ID NO:12, and the full-length amino acid sequence corresponding to this polymorphic gene is set forth in SEQ ID NO:13.

Full-Length Nucleotide Sequence of Polymorphic Human IL-1 Epsilon DNA:

```
                                              (SEQ ID NO:12)
ATGGAAAAAG CATTGAAAAT TGACACACCT CAGCGGGGGA

GCATTCAGGA TATCAATCAT CGGGTGTGGG TTCTTCAGGA

CCAGACGCTC ATAGCAGTCC CGAGGAAGGA CCGTATGTCT

CCAGTCACTA TTGCCTTAAT CTCATGCCGA CATGTGGAGA

CCCTTGAGAA AGACAGAGGG AACCCCATCT ACCTGGGCCT

GAATGGACTC AATCTCTGCC TGATGTGTGC TAAAGTCGGG

GACCAGCCCA CACTGCAGCT GAAGGAAAAG GATATAATGG

ATTTGTACAA CCAACCCGAG CCTGTGAAGT CCTTTCTCTT

CTACCACAGC CAGAGTGGCA GGAACTCCAC CTTCGAGTCT

GTGGCTTTCC CTGGCTGGTT CATCGCTGTC AGCTCTGAAG

GAGGCTGTCC TCTCATCCTT ACCCAAGAAC TGGGGAAAGC

CAACACTACT GACTTTGGGT TAACTATGCT GTTTTAA
```

Full-Length Amino Acid Sequence of Human IL-1 Epsilon:

Translation in Relevant Reading Frame (5' to 3'):

```
                                          (SEQ ID NO:13)
MEKALKIDTP QRGSIQDINH RVWVLQDQTL IAVPRKDRMS

PVTIALISCR HVETLEKDRG NPIYLGLNGL NLCLMCAKVG

DQPTLQLKEK DIMDLYNQPE PVKSFLFYHS QSGRNSTFES

VAFPGWFIAV SSEGGCPLIL TQELGKANTT DFGLTMLF*
```

The discovery of this DNA encoding IL-1 epsilon enables the construction of expression vectors comprising nucleic acid sequences encoding IL-1 epsilon polypeptides of the invention; host cells transfected or transformed with the expression vectors; biologically active human IL-1 epsilon polypeptides and molecular weight markers as isolated and purified proteins; and antibodies immunoreactive with polypeptides of the invention.

Nucleic Acid Molecules

In a particular embodiment, the invention relates to certain isolated nucleotide sequences. A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, $2^{nd}$ ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Particularly preferred nucleotide sequences of the invention are SEQ ID NO:5, SEQ ID NO:7, and SEQ ID NO:12, as set forth above. The invention further encompasses isolated fragments and oligonucleotides derived from the nucleotide sequences of SEQ ID NO:5, SEQ ID NO:7, and SEQ ID NO:12. Nucleic acid sequences within the scope of the invention include isolated DNA and RNA sequences that hybridize to the native nucleotide sequences disclosed herein under conditions of moderate or severe stringency, and which encode polypeptides or fragments thereof of the invention. These isolated DNA and RNA sequences also include full length DNA or RNA molecules encoding for IL-1 epsilon polypeptides.

As used herein, conditions of moderate stringency, as known to those having ordinary skill in the art, and as defined by Sambrook et al. *Molecular Cloning: A Laboratory Manual*, $2^{nd}$ ed. Vol. 1, pp. 1.101-104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42□C (or other similar hybridization solution, such as Stark's solution, in 50% formamide at 42□C), and washing conditions of about 60□C, 0.5×SSC, 0.1% SDS. Conditions of high stringency are defined as hybridization conditions as above, and with washing at 68□C, 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NO:5, SEQ ID NO:7, or SEQ ID NO:12, and still encode a polypeptide having the amino acid sequence of SEQ ID NO:6, SEQ ID NO:8, or SEQ ID NO:13, respectively. Such variant DNA sequences can result from silent mutations (e.g., occurring during PCR amplification) or can be the product of deliberate mutagenesis of a native sequence.

The invention thus provides equivalent isolated DNA sequences encoding polypeptides of the invention, selected from: (a) DNA derived from the coding region of a native mammalian gene; (b) cDNA comprising the nucleotide sequence of SEQ ID NO:5, SEQ ID NO:7, or SEQ ID NO:12; (c) DNA encoding the polypeptides of SEQ ID NO:6, SEQ ID NO:8, or SEQ ID NO:13; (d) DNA capable of hybridization to a DNA of (a), (b), or (c) under conditions of moderate stringency and which encodes polypeptides of the invention; and (e) DNA which is degenerate as a result of the genetic code to a DNA defined in (a), (b), (c), or (d) and which encodes polypeptides of the invention. Of course, polypeptides encoded by such equivalent DNA sequences are encompassed by the invention.

DNA that is equivalent to the DNA sequence of SEQ ID NO:5, SEQ ID NO:7, or SEQ ID NO:12 will hybridize under moderately stringent conditions to the double-stranded native DNA sequence that encode polypeptides comprising amino acid sequences of SEQ ID NO:6, SEQ ID NO:8, or SEQ ID NO:13. Examples of polypeptides encoded by such DNA, include, but are not limited to, polypeptide fragments and polypeptides comprising inactivated N-glycosylation site(s), inactivated protease processing site(s), or conservative amino acid substitution(s), as described below. Polypeptides encoded by DNA derived from other mammalian species, wherein the DNA will hybridize to the complement of the DNA of SEQ ID NO:5, SEQ ID NO:7, or SEQ ID NO:12, are also encompassed.

Expression

The nucleic acid sequence encoding polypeptides of the invention can be inserted into recombinant expression vectors using well known methods. The expression vectors include a DNA sequence of the invention operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the DNA sequence of the invention. Thus, a promoter nucleotide sequence is operably linked to a DNA sequence if the promoter nucleotide sequence controls the transcription of the DNA sequence of the invention. The ability to replicate in the desired host cells, usually conferred by an origin of replication, and a selection gene by which transformants are identified can additionally be incorporated into the expression vector.

In addition, sequences encoding appropriate signal peptides that are not naturally associated with polypeptides of the invention can be incorporated into expression vectors. For example, a DNA sequence for a signal peptide (secretory leader) can be fused in-frame to the nucleotide sequence of the invention so that the polypeptide is initially translated as a fusion protein comprising the signal peptide. A signal peptide that is functional in the intended host cells enhances extracellular secretion of the polypeptide. The signal peptide can be cleaved from the polypeptide upon secretion of polypeptide from the cell.

Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides of the invention using RNAs derived from DNA constructs disclosed herein.

Prokaryotic Systems

Prokaryotes include gram negative or gram positive organisms. Suitable prokaryotic host cells for transformation include, for example, *Escherichia coli, Bacillus subtilis, Salmonella typhimurium*, and various other species within the genera *Bacillus, Pseudomonas, Streptomyces*, and *Staphylococcus*. In a prokaryotic host cell, such as *Escherichia*

*coli*, a polypeptide of the invention can include an N-terminal methionine residue to facilitate expression of the recombinant polypeptide in the prokaryotic host cell. The N-terminal Met can be cleaved from the expressed recombinant polypeptide.

Expression vectors for use in prokaryotic host cells also generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence of the invention are inserted into the pBR322 vector. Other commercially available vectors include, for example, pKK223-3 (Pharmacia Fine Chemicals, Uppsala, Sweden) and pGEM1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

The promoter sequences commonly used for recombinant prokaryotic host cell expression vectors include beta-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *Molecular Cloning: A Laboratory Manual*, Cold Spring Harbor Laboratory, p. 412, 1982). A particularly useful prokaryotic host cell expression system employs a phage lambda $P_L$ promoter and a cI857ts thermolabile repressor sequence. Plasmid vectors available from the American Type Culture Collection, which incorporate derivatives of the lambda $P_L$ promoter, include plasmid pHUB2 (resident in *E. coli* strain JMB9 (ATCC 37092)) and pPLc28 (resident in *E. coli* RR1 (ATCC 53082)).

The DNA of the invention can be cloned in-frame into the multiple cloning site of an ordinary bacterial expression vector. Ideally the vector contains an inducible promoter upstream of the cloning site, such that addition of an inducer leads to high-level production of the recombinant protein at a time of the investigator's choosing. For some proteins, expression levels can be boosted by incorporation of codons encoding a fusion partner (such as hexahistidine) between the promoter and the gene of interest.

For expression of the recombinant protein, the bacterial cells are propagated in growth medium until reaching a pre-determined optical density. Expression of the recombinant protein is then induced, e.g., by addition of IPTG (isopropyl-b-D-thiogalactopyranoside), which activates expression of proteins from plasmids containing a lac operator/promoter. After induction (typically for 1-4 hours), the cells are harvested by pelleting in a centrifuge, e.g. at 5,000×G for 20 minutes at 4 degrees C.

For recovery of the expressed protein, the pelleted cells may be resuspended in ten volumes of 50 mM Tris-HCl (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4 degrees C. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved is removed by centrifugation (10,000×G for 20 minutes, 20□C). The protein of interest will, in most cases, be the most abundant protein in the resulting clarified supernatant. This protein may be "refolded" into the active conformation by dialysis against 50 mM Tris-HCl (pH 8)/5 MM $CaCl_2$/5 mM $Zn(OAc)_2$/1 mM GSSG/0.1 mM GSH. After refolding, purification can be carried out by a variety of chromatographic methods such as ion exchange or gel filtration. In some protocols, initial purification may be carried out before refolding. As an example, hexahistidine-tagged fusion proteins may be partially purified on immobilized nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Systems

Polypeptides of the invention alternatively can be expressed in yeast host cells, preferably from the *Saccharomyces* genus (e.g., *S. cerevisiae*). Other genera of yeast, such as *Pichia, K. lactis*, or *Kluyveromyces*, can also be employed. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980), or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene,* 107:285-195 (1991); and van den Berg et. al., *Bio/Technology,* 8:135-139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* ($Amp^r$ gene and origin of replication) into the above-described yeast vectors.

The yeast alpha-factor leader sequence can be employed to direct secretion of a polypeptide of the invention. The alpha-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad Sci. USA* 75:1929, 1978. The Hinnen et al.

protocol selects for Trp+ transformants in a selective medium, wherein the selective medium consists of 0.67% yeast nitrogen base, 0.5% casamino acids, 2% glucose, 10 µg/ml adenine, and 20 µg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian and Insect Systems

Alternatively, mammalian or insect host cell culture systems can be employed to express recombinant polypeptides of the invention. Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. *Molecular Cloning: A Laboratory Manual*, 2$^{nd}$ ed. Vol. 1-3, Cold Spring Harbor Laboratory Press, 1989. Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

Another useful expression vector, pFLAG, can be used. Flag® technology is centered on the fusion of a low molecular weight (1 kD), hydrophilic, Flag® marker peptide to the N-terminus of a recombinant protein expressed by the pFLAG-1™ Expression Vector (1) (obtained from IBI Kodak).

Polypeptides of the Invention

As noted above, the present invention also includes isolated and purified polypeptides. As used herein, the "polypeptides" of the invention refers to a genus of polypeptides that further encompasses proteins having the amino acid sequence of SEQ ID NO: 6, SEQ ID NO:8, or SEQ ID NO:13, as well as those proteins having a high degree of similarity (at least 90% homology) with such amino acid sequences and which proteins are biologically active. In addition, polypeptides of the invention refers to the gene products of the nucleotides of SEQ ID NO:5, SEQ ID NO:7, and SEQ ID NO:12.

Isolation and Purification

The term "isolated and purified" as used herein, means that the polypeptides or fragments of the invention are essentially free of association with other proteins or polypeptides, for example, as a purification product of recombinant host cell culture or as a purified product from a non-recombinant source. The term "substantially purified" as used herein, refers to a mixture that contains polypeptides or fragments of the invention and is essentially free of association with other proteins or polypeptides, but for the presence of known proteins that can be removed using a specific antibody. The term "purified" refers to either the "isolated and purified" form of polypeptides of the invention or the "substantially purified" form of polypeptides of the invention, as both are described herein.

An isolated and purified polypeptide according to the invention can be produced by recombinant expression systems as described above or purified from naturally occurring cells.

In one preferred embodiment, the expression of recombinant IL-1 epsilon polypeptides can be accomplished utilizing fusions of sequences encoding IL-1 epsilon polypeptides to sequences encoding another polypeptide to aid in the purification of polypeptides of the invention. An example of such a fusion is a fusion of sequences encoding an IL-1 epsilon polypeptide to sequences encoding the product of the *malE* gene of the pMAL-c2 vector of New England Biolabs, Inc. Such a fusion allows for affinity purification of the fusion protein, as well as separation of the maltose binding protein portion of the fusion protein from the polypeptide of the invention after purification.

The insertion of DNA encoding the IL-1 epsilon polypeptide into the pMAL-c2 vector can be accomplished in a variety of ways using known molecular biology techniques. The preferred construction of the insertion contains a termination codon adjoining the carboxyl terminal codon of the polypeptide of the invention. In addition, the preferred construction of the insertion results in the fusion of the amino terminus of the polypeptide of the invention directly to the carboxyl terminus of the Factor Xa cleavage site in the pMAL-c2 vector. A DNA fragment can be generated by PCR using DNA of the invention as the template DNA and two oligonucleotide primers. Use of the oligonucleotide primers generates a blunt-ended fragment of DNA that can be isolated by conventional means. This PCR product can be ligated together with pMAL-p2 (digested with the restriction endonuclease Xmn I) using conventional means. Positive clones can be identified by conventional means. Induction of expression and purification of the fusion protein can be performed as per the manufacturer's instructions and as noted above. This construction facilitates a precise separation of the polypeptide of the invention from the fused maltose binding protein utilizing a simple protease treatment as per the manufacturer's instructions. In this manner, purified IL-1 epsilon polypeptide can be obtained. Furthermore, such a constructed vector can be easily modified using known molecular biology techniques to generate additional fusion proteins. It is understood, of course, that many different vectors and techniques, as noted above, can be used for the expression and purification of polypeptides of the invention and that this embodiment in no way limits the scope of the invention.

Recombinant protein produced in bacterial culture is usually isolated by initial disruption of the host cells by any convenient method (including freeze-thaw cycling, sonication, mechanical disruption, or use of cell lysing agents), centrifugation, extraction from cell pellets if an insoluble polypeptide, or from the supernatant fluid if a soluble polypeptide, followed by one or more concentration, salting-out, ion exchange, affinity purification or size exclusion chromatography steps. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable polypeptide-binding proteins are anti-polypeptide antibodies, and other proteins that are capable of high-affinity binding of polypeptides of the invention. A preferred polypeptide-binding protein is an anti-polypeptide monoclonal antibody.

In a preferred embodiment, transformed yeast host cells are employed to express polypeptides of the invention as a secreted polypeptide in order to simplify purification. Secreted recombinant polypeptide from a yeast host cell fermentation can be purified by methods analogous to those disclosed by Urdal et al. (*J. Chromatog.* 296:171, 1984) (relating to the use of two sequential, reversed-phase HPLC steps for purification).

Variants

The invention also includes variants of the polypeptides of the invention. A polypeptide "variant" as referred to herein means a polypeptide substantially homologous to native polypeptides of the invention, but which has an amino acid sequence different from that of native polypeptides (human, murine or other mammalian species) of the invention because of one or more deletions, insertions or substitutions. The variant amino acid sequence preferably is at least 80% identical to a native polypeptide amino acid sequence. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events, proteolytic cleavage of the IL-1 epsilon polypeptides, or transcription/translation from different alleles. Variations attributable to proteolysis include, for example, differences in the N or C-termini upon expression in different types of host cells, due to proteolytic removal of one or more terminal amino acids from the polypeptides (generally from 1-5 terminal amino acids) of the invention.

Oligomers

The polypeptides of the invention can also exist as oligomers, such as covalently linked or non-covalently linked dimers or trimers. Oligomers can be linked by disulfide bonds formed between cysteine residues on different polypeptides.

In one embodiment of the invention, a polypeptide dimer is created by fusing polypeptides of the invention to the Fc region of an antibody (e.g., IgG1) in a manner that does not interfere with the biological activity of these polypeptides. The Fc region preferably is fused to the C-terminus of a soluble polypeptide of the invention, to form an Fc fusion or an Fc polypeptide. The terms "Fc fusion protein" or "Fc polypeptides" as used herein includes native and mutein forms, as well as truncated Fc polypeptides containing the hinge region that promotes dimerization. Exemplary methods of making Fc polypeptides set forth above are disclosed in U.S. Pat. Nos. 5,426,048 and 5,783,672, both of which are incorporated herein by reference.

General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the polypeptide:Fc fusion protein of the invention is inserted into an appropriate expression vector. Polypeptide:Fc fusion proteins are allowed to assemble much like antibody molecules, whereupon interchain disulfide bonds form between Fc polypeptides, yielding divalent polypeptides of the invention. If fusion proteins are made with both heavy and light chains of an antibody, it is possible to form a polypeptide oligomer with as many as four polypeptides extracellular regions. Alternatively, one can link two soluble polypeptide domains with a peptide linker.

Alterations

As stated above, the invention provides isolated and purified polypeptides, and fragments thereof, both recombinant and non-recombinant. Variants and derivatives of native polypeptides can be obtained by mutations of nucleotide sequences coding for native polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

Polypeptides of the invention can also be modified to create polypeptide derivatives by forming covalent or aggregative conjugates with other chemical moieties, such as glycosyl groups, polyethylene glycol (PEG) groups, lipids, phosphate, acetyl groups and the like. Covalent derivatives of polypeptides of the invention can be prepared by linking the chemical moieties to functional groups on polypeptide amino acid side chains or at the N-terminus or C-terminus of a polypeptide of the invention or the extracellular domain thereof. Other derivatives of polypeptides within the scope of this invention include covalent or aggregative conjugates of these polypeptides or peptide fragments with other proteins or polypeptides, such as by synthesis in recombinant culture as N-terminal or C-terminal fusions. For example, the conjugate can comprise a signal or leader polypeptide sequence (e.g. the alpha-factor leader of *Saccharomyces*) at the N-terminus of a polypeptide of the invention. The signal or leader peptide co-translationally or post-translationally directs transfer of the conjugate from its site of synthesis to a site inside or outside of the cell membrane or cell wall.

Polypeptide conjugates can also comprise peptides added to facilitate purification and identification of polypeptides of the invention. Such peptides include, for example, poly-His or the antigenic identification peptides described in U.S. Pat. No. 5,011,912 and in Hopp et al., *Bio/Technology* 6:1204, 1988.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, equivalent DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Fragments and Uses Thereof

In yet another aspect of the invention, the polypeptides of the invention can be subjected to fragmentation into peptides by chemical and enzymatic means.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50, 1981; T. Masaki et al., *Biochim. Biophys. Acta* 660:51-55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102-1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. Consistent polypeptides and peptide fragments can be obtained by pretreating with N-glycanase to remove glycosylation, or expressing the polypeptides in bacterial hosts.

The polypeptides and fragments thereof can also be varied by fusing additional peptide sequences to either or both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure.

Finally, as to the kits that are encompassed by the invention, the constituents of such kits can be varied, but typically contain the polypeptide and fragments thereof. Kits can further contain antibodies directed against polypeptides or fragments thereof of the invention.

Sense and Antisense Oligonucleotides

In yet another embodiment of the invention, antisense or sense oligonucleotides comprising a single-stranded nucleic acid sequence (either RNA or DNA) capable of binding to a target mRNA sequence (forming a duplex) or to the sequence in the double-stranded DNA helix (forming a triple helix) can be made according to the invention. Antisense or sense oligonucleotides, according to the present invention, comprise a fragment of the coding region of cDNA (SEQ ID NO:5, SEQ ID NO:7, or SEQ ID NO:12). Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus can be used to block expression of polypeptides of the invention. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation), but retain sequence specificity to be able to bind to target nucleotide sequences. Other examples of sense or antisense oligonucleotides include those oligonucleotides that are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides can be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Alternatively, sense or antisense oligonucleotides also can be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

In yet another embodiment, a sense or an antisense oligonucleotide can be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Chromosome Mapping

In still another embodiment, oligonucleotides representing all or a portion of SEQ ID NO:5, SEQ ID NO:7, or SEQ ID NO:12 can be used by those skilled in the art using well-known techniques to identify the human chromosome 2, and the specific locus thereof, that contains the DNA of IL-1 family members, for example, IL-1 epsilon. As set forth below, SEQ ID NO:5, SEQ ID NO:7, and SEQ ID NO:12 have been mapped by radiation hybrid mapping to the long arm (2q) region of chromosome 2. That region is associated with specific diseases which include but are not limited to glaucoma, ectodermal dysplasia, insulin-dependent diabetes mellitus, wrinkly skin syndrome, T-cell leukemia/lymphoma, asthma, and tibial muscular dystrophy. Thus, SEQ ID NO:5, SEQ ID NO:7, SEQ ID NO:12, or a fragment of these sequences can be used by one skilled in the art using well-known techniques to study the above described diseases and other abnormalities relating to chromosome 2. This would enable one to distinguish conditions in which this marker is rearranged or deleted. In addition, SEQ ID NO:5, SEQ ID NO:7, SEQ ID NO:12, or a fragment thereof can be used as a positional marker to map other human genes of unknown location.

Therapeutic and Research Uses

Another embodiment of the invention relates to therapeutic uses of IL-1 epsilon. IL-1 ligands play a central role in protection against infection and in promoting immune and inflammatory responses, which includes cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. With the continued increase in the number of known IL-1 family members, a suitable classification scheme is one based on comparing polypeptide structure as well as function (activation and regulatory properties). Thus, IL-1 epsilon, like IL-1 alpha, IL-1 beta, and IL-18, would likely be involved in many of the functions noted above as well as promote inflammatory responses and therefore perhaps be involved in the causation and maintenance of inflammatory and/or autoimmune diseases such as rheumatoid arthritis (and/or other arthritic conditions that have an inflammatory or autoimmune component, for example, ankylosing spondylitis), inflammatory bowel disease (including Crohn's Disease and ulcerative colitis), and psoriasis (including psoriatic arthritis). Other inflammatory and/or autoimmune diseases in which IL-1 epsilon?????? may be implicated include asthma (and other pulmonary conditions relating to an immune or inflammatory response and/or in which airway hyperreactivity plays a role), and multiple sclerosis (and/or other demyelinating conditions that have an inflammatory or autoimmune component). As such, alterations in the expression and/or activation of IL-1 family members such as IL-1 epsilon can have profound effects on a plethora of cellular processes, including, but not limited to, activation or inhibition of cell specific responses, proliferation, and inflammatory reactions based on changes in signal transduction.

Accordingly, IL-1 epsilon has therapeutic uses, such as protecting against infection and generating immune and inflammatory responses in individuals whose immune and inflammatory responses are inappropriate or nonresponsive. For example, IL-1 epsilon may be useful in stimulating the immune system of individuals whose immune system is immunosuppressed. Similarly, because IL-1 epsilon likely promotes inflammatory responses and is involved in the causation and maintenance of inflammatory and/or autoimmune diseases, antagonists of IL-1 epsilon are useful in inhibiting or treating inflammatory and/or autoimmmune disease. Thus, antagonists of IL-1 epsilon will be useful in treating as rheumatoid arthritis, inflammatory bowel disease, and psoriasis.

IL-1 mediated cellular signaling often involves a molecular activation cascade, during which a receptor propagates a ligand-receptor mediated signal by specifically activating intracellular kinases which phosphorylate target substrates, resulting in the activation of the transcription factor NFkappaB and the protein kinases Jun N-terminal kinase and p38 map kinase. These substrates can themselves be kinases which become activated following phosphorylation. Alternatively, they can be adaptor molecules that facilitate downstream signaling through protein-protein interaction following phosphorylation.

Given the data presented in Example III, below, it is likely that IL-1 epsilon is an agonist, such as, for example IL-1 alpha or IL-18. As stated above, such agonists are useful in promoting immune and inflammatory responses in individuals whose own immune systems are inappropriately under responsive. Antagonists of IL-1 epsilon will be useful in treating or ameliorating conditions in which the immune and/or inflammatory response is over responsive. For purposes of antagonizing IL-1 epsilon activity, inhibitors of IL-1 epsilon can be engineered or designed using techniques known in the art.

Antagonists of IL-1 epsilon will be useful in treating arthritic conditions that have an inflammatory or autoimmune component, for example, rheumatoid arthritis and/or ankylosing spondylitis: inflammatory bowel disease, including Crohn's Disease and ulcerative colitis, and psoriasis (including psoriatic arthritis). Other inflammatory and/or autoimmune diseases in which IL-1 epsilon is implicated include pulmonary conditions relating to an immune or inflammatory response and/or in which airway hyperreactivity plays a role, for example. asthma, infection-associated airway hyperactivity, granuloniatous lung disease, emphysema and chronic fibrosing alveolitis and acute hyperoxic lung damage, and demyelinating conditions that have an inflammatory or autoimmune component, for example, multiple sclerosis and/or chronic inflammatory demyelinating polyneuropathy. Antagonists of IL-1 epsilon will also be useful in ameliorating these conditions.

Additional conditions for which an autoimmune and/or inflammatory component is a contributory factor (and thus, for which antagonists of IL-1 epsilon are useful) include cardiovascular conditions such as stroke, acute myocardial infarction, unstable angina, arterial restenosis and congestive heart failure. IL-1 epsilon antagonists are useful in treating or preventing osteoporosis and/or osteoarthritis, as well as glomerulonephritis, uveitis, and/or Behçet's syndrome. An autoimmune or inflammatory component also plays a role in the cause or maintenance of sepsis, acute pancreatitis, diabetes (particularly Type II, insulin dependent diabetes), endometriosis, and periodontal disease. Similarly, the inflammatory response causes or exacerbates heat stroke and glaucoma, and the cytokines involved in the immune/inflammatory response play a supportive role in neoplastic disease (for example, in multiple myeloma and/or myeloid leukemia), facilitating the growth of neoplastic cells. Accordingly, antagonists of IL-1 epsilon are useful in treating or ameliorating these conditions by downregulating the immune and/or inflammatory response that plays a causative role therein.

The compositions of the present invention, including IL-1 epsilon inhibitors, can be introduced into the extracellular environment by well-known means, such as by administering the protein intravenously or by coupling it to a monoclonal antibody targeted to a specific cell type, to thereby affect signaling. When used as a therapeutic agent, polypeptides of the invention can be formulated into pharmaceutical compositions according to known methods. The compositions can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of polypeptides of the invention.

The dosage of the composition can be readily determined by those of ordinary skill in the art. The amount to be administered and the frequency of administration can be determined empirically and will take into consideration the age and size of the patient being treated, as well as the malady being treated.

Treatment comprises administering the composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The composition may also be given locally, such as by injection into the particular area, either intramuscularly or subcutaneously.

In addition, the DNA, polypeptides, and antibodies against polypeptides of the invention can be used as reagents in a variety of research protocols. A sample of such research protocols are given in Sambrook et al. *Molecular Cloning: A Laboratory Manual*, $2^{nd}$ ed. Vol. 1-3, Cold Spring Harbor Laboratory Press, (1989). For example, these reagents can serve as markers for cell-specific or tissue-specific expression of RNA or proteins. Similarly, these reagents can be used to investigate constitutive and transient expression of RNA or polypeptides. As noted above, the DNA can be used to determine the chromosomal location of DNA and to map genes in relation to this chromosomal location. The DNA can also be used to examine genetic heterogeneity and heredity through the use of techniques such as genetic fingerprinting, as well as to identify risks associated with genetic disorders. The DNA can be further used to identify additional genes related to the DNA and to establish evolutionary trees based on the comparison of sequences. The DNA and polypeptides can be used to select for those genes or proteins that are homologous to the DNA or polypeptides, through positive screening procedures such as Southern blotting and immunoblotting and through negative screening procedures such as subtraction.

Further, because IL-1 epsilon is a ligand, it takes part in protein-protein interactions with at least one or more proteins, i.e. its receptor(s). Thus, the polypeptides and fragments of the invention can be used as reagents to identify (a) proteins that the polypeptide regulates, and (b) proteins with which it might interact. Therefore, IL-1 epsilon ligands or polypeptides comprising portions of an IL-1 epsilon ligand could be used by coupling recombinant protein to an affinity matrix, or by using them as "baits" in the yeast 2-hybrid system according to well established molecular biology techniques, to identify proteins that interact directly with the polypeptide of the invention. Further, the IL-1 epsilon polypeptides and fragments of the present invention find use in studies directed toward discovering IL-1 receptors and/or IL-1 epsilon receptors. For example, IL-1 epsilon polypeptides and IL-1 epsilon polypeptide fragments can be used in binding studies to identify receptor-expressing cells. Suitable binding studies are known in the art and are well within the knowledge of those skilled in the art. Similarly, the IL-1 epsilon polypeptides and polypeptide fragments of the present invention find additional uses in cloning receptors using expression cloning techniques.

The polypeptides and fragments thereof can also be used as reagents in the study of signaling pathways utilized by IL-1 and IL-1R homologs or family members, and/or in blocking those signaling pathways. Such novel IL-1 receptor homologs can be specifically used as reagents to identify novel molecules involved in signal transduction pathways, characterize cell and tissue expression, understand their roles in development, immune, and inflammatory responses, and identify regulatory molecules and physiologically relevant protein substrates.

Alternatively, polypeptides of the invention could be engineered prior to expression with a tag such as poly-His or Flag®, then be expressed and purified using either nickel chelate chromatography or anti-Flag® antibody coupled to a resin, respectively. Once bound to the resin, the polypeptide of the invention could be covalently attached using a bifunctional cross-linking agent using well established techniques. The covalently bound polypeptide to the resin could then be used to purify molecules from cell lysates or cell supernatants (following treatment with various reagent) through their affinity for the polypeptide of the invention.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a DNA encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*Proc. Natl. Acad. Sci. USA* 84:3439, 1987), Larrick et al. (*Bio/Technology* 7:934, 1989), and Winter and Harris (*TIPS* 14:139, May, 1993).

In addition to antibodies that can be produced via recombinant methods, human antibodies can be produced in animals that have been genetically manipulated to have human immunoglobulin genes (transgenic animals). Procedures to generate antibodies transgenically can be found in GB 2,272,440, U.S. Pat. Nos. 5,569,825 and 5,545,806 and related patents claiming priority therefrom, all of which are incorporated by reference herein. Preferably, for use in humans, the antibodies are human or humanized; techniques for creating such human or humanized antibodies are also well known and are commercially available from, for example, Medarex Inc. (Princeton, N.J.) and Abgennix Inc. (Fremont, Calif.).

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Drug Discovery

The purified polypeptides according to the invention will facilitate the discovery of inhibitors (or antagonists) and/or agonists of such polypeptides. The use of a purified polypeptide of the invention in the screening of potential inhibitors and/or agonists thereof is important and can eliminate or reduce the possibility of interfering reactions with contaminants.

In addition, polypeptides of the invention can be used for structure-based design of polypeptide-inhibitors. Such structure-based design is also known as "rational drug design." The polypeptides can be three-dimensionally analyzed by, for example, X-ray crystallography, nuclear magnetic resonance or homology modeling, all of which are well-known methods. The use of the polypeptide structural information in molecular modeling software systems to assist in inhibitor design and inhibitor-polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of polypeptides of the invention for likely binding sites of substrates, synthesizing a new molecule that incorporates a predictive reactive site, and assaying the new molecule as described above.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Homogeneous assays are preferred. Also comprehended herein are cell-based assays, for example those utilizing reporter genes, as well as functional assays that analyze the effect of an antagonist or agonist on biological function(s) or activity (ies) of IL-1 epsilon (for example, secretion of cytokines as disclosed herein).

Accordingly, in one aspect of the invention, there is provided a method for screening a test compound to determine whether the test compound affects a biological activity of an IL-1 epsilon polypeptide, the method comprising contacting the test compound and the IL-1 epsilon polypeptide with cells capable of exhibiting the biological activity when contacted with IL-1 epsilon, and analyzing the cells for the occurrence of the biological activity, wherein if the biological activity observed in the presence of the test compound differs from the biological activity that is observed when the test compound is absent, the test compound affects the biological activity of the IL-1 epsilon.

As used herein, the IL-1 epsilon polypeptide comprises a polypeptide selected from the group consisting of the polypeptides of SEQ ID NO:6, SEQ ID NO:8, and SEQ ID NO:13, and polypeptides encoded by DNAs that hybridize under moderately stringent conditions to the DNAs of SEQ ID NO:5, SEQ ID NO:7, or SEQ ID NO:12. Such polypeptides include polypeptides comprising variant amino acid sequences that are at least 80% identical to the polypeptides of SEQ ID NO:6, SEQ ID NO:8, or SEQ ID NO:13 (preferably, the variant amino acid sequences that are at least 90% identical, more preferably at least 95% identical, most preferably at least 97% identical, to the polypeptides of SEQ ID NO:6, SEQ ID NO:8, or SEQ ID NO:13). Additional examples of useful IL-1 epsilon polypeptides include polypeptides comprising the amino acid sequences of SEQ ID NOs:6, 8, or 13 wherein the polypeptides comprise alterations to the amino acid sequences selected from the group consisting of inactivated N-glycosylation site(s), inactivated protease processing site(s), conservative amino acid substitution(s), and combinations thereof. Moreover, fragments of the aforesaid polypeptides that have at least one activity of IL-1 epsilon as described below are also comprehended herein (for example, a fragment as shown in FIG. 4).

IL-1 epsilon biological activity includes, but is not limited to, IL-1 epsilon induced cytokine expression, IL-1 epsilon induced expression of molecules indicative of activation of an immune or inflammatory response (for example, COX2, iNOS), IL-1 epsilon induced cell-surface molecule expression, activation of one or more signaling cascades, induction of mRNAs for the aforementioned proteins, induction of cell proliferation and/or cell death, induction of morphological and/or functional changes in cells, and combinations thereof.

The inventive methods comprise methods of assaying for any of these biological activities. When the methods of the present invention include assaying for IL-1 epsilon induced cytokine expression, cytokines that may be assayed include (but are not limited to) IL-1 alpha, IL-1 beta, TNF-alpha, IL-10, IFN-gamma, IL-12 (in particular, the p40 subunit), IL-6, IL-1ra, IL4, IL-13, GM-CSF, IL-18, IL-1 homologs such as IL-1 delta, IL-1 eta, IL-1 theta, IL-1 zeta, and IL-1 H1, and combinations thereof. Similarly, when the screening methods of the present invention include assaying for IL-1 epsilon induced cell surface molecule expression, the cell surface molecules that may be assayed include ICAM-1, TLR4, TLR5, TLR9, DC-B7, MHC class I and II antigens, VCAM, ELAM, B7-1, B7-2, CD40L, and combinations thereof.

IL-1 epsilon mediated activation of signaling pathways often involves a cascade of molecular changes, for example as discussed previously wherein a receptor propagates a ligand-receptor mediated signal by specifically activating intracellular kinases which phosphorylate target substrates (which can themselves be kinases that become activated following phosphorylation, or adaptor molecules that facilitate down-stream signaling through protein-protein interaction following phosphorylation), resulting in the activation of other factors (for example, NFkappaB). When the screening methods of the present invention include assaying for IL-1 epsilon induced activation of signaling pathways, the signaling pathways that may be assayed include those involving activation of NFkappaB. Assaying for activation signaling cascades further includes detecting phosphorylation of molecules that occurs during the signaling cascade, as in the phosphorylation of IkappaB (including IkappaB degradation assays, and assays for free IkappaB), p38 MAP kinase, and Stress-Activated Protein Kinase (SAPK/JNK).

Moreover, those of skill in the art understand that biological activity(ies) is/are most often induced by the binding of a ligand (i.e., IL-1 epsilon) to a receptor (counterstructure or binding moiety) present on a cell; accordingly, as previously described, IL-1 epsilon polypeptides (including IL-1 epsilon polypeptide fragments) can be used in binding studies to identify receptor-expressing cells. Such binding studies also provide assays useful in the inventive methods. IL-1 epsilon polypeptides may also be used to clone receptors (or other molecules that bind IL-1 epsilon) and to screen for molecules that block receptor/ligand interactions. Those of ordinary skill in the art further understand that biological activities include cell proliferation, cell death, and changes in cell morphology and/or function (for example, activation, maturation); assays that evaluate such effects of IL-1 epsilon are known in the art, and will also be useful in the inventive methods.

The inventive methods further encompass performing more than one assay to discover and/or analyze agonists or antagonists of IL-1 epsilon activity (i.e., combination methods). Generally, such methods comprise selecting test compounds that affect a property of IL-1 epsilon (i.e., an ability of IL-1 epsilon to bind an IL-1 epsilon counter structure), then testing the selected compounds for an effect on another property of IL-1 epsilon (i.e., contacting the selected test compounds and an IL-1 epsilon polypeptide with cells capable of exhibiting a biological activity when contacted with IL-1 epsilon, and determining whether the compounds affect the biological activity. For example, the inventive methods may comprise a first assay to determine whether a candidate molecule interacts with (binds to) IL-1 epsilon. Preferably, the first assay is in a high throughput format, numerous forms of which are known in the art and disclosed herein. Such an assay will generally comprise the steps of: contacting test compounds and an IL-1 epsilon polypeptide with an IL-1 epsilon counterstructure; determining whether the test compounds affect the ability of IL-1 epsilon to bind the counterstructure; and selecting one or more test compounds that affect the ability of IL-1 epsilon to bind the counterstructure. The inventive combination methods further comprise evaluating selected compounds in a second assay, for agonistic or antagonistic effect on biological activity using one or more of the aforementioned assays.

Alternatively, the inventive combination methods may comprise a first assay to determine whether a candidate molecule modulates a biological activity of IL-1 epsilon, as described herein. According to such combination methods, molecules that modulate an IL-1 epsilon biological activity in this manner are selected using one or more of the aforementioned assays for biological activity, and assayed to determine whether the candidate molecule(s) bind IL-1 epsilon. The selected molecules may be tested to further define the exact region or regions of IL-1 epsilon to which the test molecule binds (for example, epitope mapping for antibodies).

As disclosed previously, the types of assays for biological activities of IL-1 epsilon that can be used in the inventive combination methods include assays for the expression of cytokines, assays for the expression of cell-surface molecules, assays to detect activation of signaling molecules, assays to detect induction of mRNAs, and assays that evaluate cell proliferation or cell death (and combinations thereof), as described herein. Molecules that bind and that have an agonistic or antagonistic effect on biologic activity will be useful in treating or preventing diseases or conditions with which the polypeptide(s) are implicated.

Those of ordinary skill in the art understand that when the biological activity observed in the presence of the test compound is greater than that observed when the test compound is absent, the test compound is an agonist of IL-1 epsilon, whereas when the biological activity observed in the presence of the test compound is less than that observed when the test compound is absent, the test compound is an antagonist (or inhibitor) of IL-1 epsilon. Generally, an antagonist will decrease or inhibit, an activity by at least 30%; more preferably, antagonists will inhibit activity by at least 50%, most preferably by at least 90%. Similarly, an agonist will increase, or enhance, an activity by at least 20%; more preferably, agonists will enhance activity by at least 30%, most preferably by at least 50%. Those of skill in the art will also recognize that agonists and/or antagonists with different levels of agonism or antagonism respectively may be useful for different applications (i.e., for treatment of different disease states).

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic. Several useful assays are disclosed in U.S. Ser. No. 09/851,673, filed May 8, 2001 (the relevant disclosure of which is hereby incorporated by reference).

Candidate Molecules to be Tested for Modulation of IL-1 Epsilon Activity:

The methods of the invention may be used to identify antagonists (also referred to as inhibitors) and agonists of IL-1 epsilon activity from cells, cell-free preparations, chemical libraries, cDNA libraries, recombinant antibody libraries (or libraries comprising subunits of antibodies) and natural product mixtures. The antagonists and agonists may be natural or modified substrates, ligands, enzymes, receptors, etc. of the polypeptides of the instant invention, or may be structural or functional mimetics of IL-1 epsilon or its binding partner/counterstructure. Potential antagonists of the instant invention may include small molecules, peptides and antibodies that bind to and occupy a binding site of the inventive polypeptides or a binding partner thereof, causing them to be unavailable to bind to their natural binding partners and therefore preventing normal biological activity. Antagonists also include chemicals (including small molecules and peptides) that interfere with the signaling pathways used by IL-1 epsilon (for example, by inhibiting the interaction of receptor subunits, or inhibiting the interaction of intracellular components of the signaling cascade). Potential agonists include small molecules, peptides and antibodies which bind to the instant polypeptides or binding partners thereof, and elicit the same or enhanced biologic effects as those caused by the binding of the polypeptides of the instant invention. Moreover, substances that activate (or enhance) the signaling pathways used by IL-1 epsilon are also included within the scope of agonists of IL-1 epsilon.

Small molecule agonists and antagonists are usually less than 10K molecular weight and may possess a number of physicochemical and pharmacological properties which enhance cell penetration, resist degradation and prolong their physiological half-lives (Gibbs, J., Pharmaceutical Research in Molecular Oncology, Cell, Vol. 79 (1994)). Antibodies, which include intact molecules as well as fragments such as Fab and F(ab')2 fragments, as well as recombinant molecules derived therefrom (including antibodies expressed on phage, intrabodies, single chain antibodies such as scFv and other molecules derived from immunoglobulins that are known in the art), may be used to bind to and inhibit the polypeptides of the instant invention by blocking the propagation of a signaling cascade. It is preferable that the antibodies are humanized, and more preferable that the antibodies are human. The antibodies of the present invention may be prepared by any of a variety of well-known methods.

Additional examples of candidate molecules, also referred to herein as "test molecules" or "test compounds," to be tested for the ability to modulate IL-1 epsilon activity include, but are not limited to, carbohydrates, small molecules (usually organic molecules or peptides), proteins, and nucleic acid molecules (including oligonucleotide fragments typically consisting of from 8 to 30 nucleic acid residues). Peptides to be tested typically consist of from 5 to 25 amino acid residues. Also, candidate nucleic acid molecules can be antisense nucleic acid sequences, and/or can possess ribozyme activity.

Small molecules to be screened using the hereindescribed screening assays can typically be administered orally or by injection to a patient in need thereof. Small molecules that can be administered orally are especially preferred. The small molecules of the invention preferably will not be toxic (or only minimally toxic) at the doses required for them to be effective as pharmaceutical agents, and they are preferably not subject to rapid loss of activity in the body, such as the loss of activity that might result from rapid enzymatic or chemical degradation. In addition, pharmaceutically useful small molecules are preferably not immunogenic.

The methods of the invention can be used to screen for antisense molecules that inhibit the functional expression of one or more mRNA molecules that encode one or more proteins that mediate an IL-1 epsilon-dependent cellular response. An anti-sense nucleic acid molecule is a DNA sequence that is capable of can hybridizing to the target mRNA molecule through Watson-Crick base pairing, and inhibiting translation thereof. Alternatively, the DNA may be inverted relative to its normal orientation for transcription and so express an RNA transcript that is complementary to the target mRNA molecule (i.e., the RNA transcript of the anti-sense nucleic acid molecule can hybridize to the target mRNA molecule through Watson-Crick base pairing). An anti-sense nucleic acid molecule may be constructed in a number of different ways provided that it is capable of interfering with the expression of a target protein. Typical anti-sense oligonucleotides to be screened preferably are 30-40 nucleotides in length. The anti-sense nucleic acid molecule generally will be substantially identical (although in antisense orientation) to the target gene. The minimal identity will typically be greater than about 80%, but a higher identity might exert a more effective repression of expression of the endogenous sequences. Substantially greater identity of more than about 90% is preferred, though about 95% to absolute identity would be most preferred.

Candidate nucleic acid molecules can possess ribozyme activity. Thus, the methods of the invention can be used to screen for ribozyme molecules that inhibit the functional expression of one or more mRNA molecules that encode one or more proteins that mediate an IL-1 epsilon dependent cellular response. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

The design and use of target RNA-specific ribozymes is described in Haseloff et al. (*Nature,* 334:585, 1988; see also U.S. Pat. No. 5,646,023), both of which publications are incorporated herein by reference. Tabler et al. (*Gene* 108: 175, 1991) have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family if the cleavage sites are conserved.

The following examples are presented to promote a fuller understanding of this invention. These examples do not, however, limit the scope of the invention.

EXAMPLE I

Isolation and Identification of a New Human IL-1 Ligand

We screened a human genomic phage library (Stratagene catalog # 946205) using a mixture of $^{32}$P-labeled single-strand DNA probes corresponding to the entire coding sequence of murine IL-1 epsilon. After low stringency washing (low stringency washing is defined as 0.2×SSC/ 0.1% SDS, at room temperature, Ausubel et al. *Current Protocols in Molecular Biology*, Vol. 2, p. 10.3, John Wiley & Sons, Inc., (1996)), a positive clone with a strong hybridization signal was identified. DNA made from this clone and subjected to Southern analysis identified a 5.5 kb Sal I-Asp 718 restriction fragment which was subcloned into pBluescript and sequenced. Homology analysis of the 5.5 kb fragment using the UWGCG computer program "bestfit" revealed that a 212 bp region within the clone was 74% similar at the nucleotide level to the 3 prime exon of murine IL-1 epsilon. As set forth in FIG. 3, this 212 bp sequence contains an open reading frame of 70 amino acids with 66% similarity (64% identity) to the 3 prime exon of murine IL-1 epsilon.

The genomic sequence around the human IL-1 epsilon locus was extended another 5 kb in the 5' direction using a Genome Walking kit (available from Clonetech) in accordance with manufacturer's instructions. Analysis of the sequence of this upstream region revealed three additional putative exons. RT-PCR was used to confirm the expression of these exons, and their linkage into a single IL-1 epsilon cDNA, in RNA from four different human tissue sources (thymus, tonsil, and the cell lines HL-60 and THP-1). Additionally, a cDNA clone was obtained from the Stratagene Universal Human cDNA Library Array I that also demonstrated the joining of the three 3'-most exons. The cDNA clone from the Universal Human cDNA Library Array I was a partial clone that did not extend to the 5' end of the open reading frame. Full-length human IL-1 epsilon DNA sequences are disclosed in SEQ ID NO:7 and SEQ ID NO:12. The polypeptides encoded by SEQ ID NO:7 and SEQ ID NO:12 are disclosed in SEQ ID NO:8 and SEQ ID NO:13, respectively. As set forth in FIG. 4, amino acids 51-159 of SEQ ID NO:8 and SEQ ID NO:13 share 53% similarity (49% identity) with the murine IL-1 epsilon (long form).

EXAMPLE II

Chromosome Mapping of Human IL-1 Epsilon by Radiation Hybrid Mapping

PCR was performed using the Whitehead Institute/MIT Center for Genome Research Genebridge4 panel of 93 radiation the Whitehead Institute/MIT Center for Genome Research Genebridge4 panel of 93 radiation hybrids which can be found by navigating to the Whitehead Institute/MIT website (www-genome.wi.mit, with an 'edu' extension), searching the site for genebridge4. Primers were used which lie within the putative 3 prime exon of human IL-1 epsilon and which amplify a 195 bp, product from human genomic DNA, but do not amplify hamster genoniic DNA. The results of the PCRs were converted into a data vector that was submitted to the Whitehead/MIT Radiation Mapping site on the internet (www-seq.wi.mit, with an 'edu' extension). The data was scored and the chromosomal assignment and placement relative to known Sequence Tag Site (STS) markers on the radiation hybrid map provided. According to die results, human IL-1 epsilon lies on chromosome 2, at 11.54 cR from STS D2S121 and 4.3 cR from the marker CRLC.GAAT11C03. The Whitehead Institute/MIT web site provides additional information about radiation hybrid mapping.

EXAMPLE III

Activation of Signaling Molecules in Human Cells by Human IL-1 Epsilon

The following describes tests and results that were carried out to determine whether Il-1 epsilon is capable of activating some of the same signaling molecules involved in stress responses as are activated by IL-1 alpha, IL-1 beta and other inflammatory cytokines.

Human IL-1 epsilon was transfected into COS-1 cells. Several days after the transfection, conditioned medium (containing the transiently expressed IL-1 epsilon) was harvested. Test cells were incubated with this conditioned medium, or alternatively with conditioned medium from COS-1 cells transfected with the empty expression vector. Approximately 10 minutes following the incubation, cell extracts were prepared from the test cells, and the presence of activated signaling molecules was assayed by the use of antibodies specific for the phosphorylated forms of IKBalpha (phosphorylation on Ser32), p38 MAP kinase (phosphorylation on Thr180 and Tyr182), and Stress-Activated Protein Kinase (SAPK/JNK) (phosphorylation on Thr183/Tyr185) (the antibodies were obtained from New England Biolabs, Beverly, Mass.). These signal transduction molecules are known to be involved in a wide range of cellular responses to stimuli such as UV irradiation, endotoxin, and inflammatory cytokines including IL-1 beta. Compared to control conditioned medium, conditioned medium containing human Il-1 epsilon activated IKBalpha and p38 MA kinase phosphorylation in a number of human cell lines including Human Foreskin Fibroblasts and Human Umbelical Vein Endothelial Cells (ATCC CRL-1730). In the non-Hodgkins lymphoma cell line K299, human IL-1 epsilon specifically activated JNK/SAPK phosphorylation. These results demonstrate that IL-1 epsilon is involved in stress response signaling pathways.

EXAMPLE IV

Tissue Distribution of Human IL-1 Epsilon

The tissue distribution of human IL-1 epsilon mRNA was investigated using PCR amplification from a panel of first strand cDNA templates. Specifically, a Clontech (Palo Alto, Calif.) Human Multiple Tissue cDNA Panel was screened using a forward primer in exon 2 and a reverse primer in exon 4, which, together, amplify a 450 base-pair fragment of IL-1 epsilon. The PCR reaction was run for 35 cycles with an annealing temperature of 60 degrees C. PCR products were detected on an agarose gel using ethidium bromide.

Human IL-1 epsilon mRNA was detected in the spleen, lymph node, thymus, tonsil, and leukocyte tissues. The tissue with the highest levels of human IL-1 epsilon mRNA is tonsil. Moreover, human IL-1 epsilon mRNA was also detected in small airway epithelium under certain conditions (in proliferative and *Yersinia*-infected, but not quiescent, cells), as well as in the human cell lines MoT, HUT-102, Raji, THP-1, IMTLH, HL60, and HPT-4. Low levels of mRNA were detected in colon tissue as well as the colon cell line T84, and in HUVEC treated with PMA and ionomycin. The HaCAT keratinocyte cell line also expressed IL-1 epsilon mRNA after treatment with LPS, IL-1/TNF/IL-18, or ultraviolet light (at 30 seconds).

Expression of IL-1 epsilon was also analyzed in several animal models of human disease by conventional real-time polymerase chain reaction (RT-PCR) substantially as described in U.S. Ser. No. 09/876,790, filed Jun. 6, 2001, and/or by TaqMan® RT-PCR (Applied Biosystems, Foster City, Calif.). Total RNA from small or large intestine (colitis models: DSS-induced colitis, anti-CD-3 induced colitis and MdrKO spontaneous colitis), spinal cord (multiple sclerosis [MS] models: EAE using SJL mice injected with PLP), or lung (asthma model: BALB/c/OVA-induced asthma model) was used to make first strand cDNA. The level of expression was subjectively scored as a function of relative ethidium bromide staining intensity.

Results of these experiments indicated that IL-1 epsilon was upregulated in DSS-induced colitis in C57BL/6 mice, but not in BALB/c mice, or in anti-CD3 induced ileitis. Additionally, the expression of IL-1 epsilon was upregulated in MdrKO mice that developed spontaneous colitis. Accordingly, IL-1 epsilon is implicated in the cause or prolongation of inflammatory bowel disease, and antagonists thereof will be useful in treating or ameliorating inflammatory bowel disease in individuals afflicted with such conditions. Additionally, IL-1 epsilon was also upregulated in the OVA-induced asthma model, indicating that an antagonist thereof may be useful in treating or ameliorating asthma and other pulmonary conditions relating to an immune or inflammatory response.

EXAMPLE V

Activation of ICAM-1 Levels in Human Cells by Human IL-1 Epsilon

The following describes tests and results that were carried out to determine whether Il-1 epsilon is capable of activating some of the same cell surface molecules involved in stress responses as are activated by IL-1 alpha, IL-1 beta and other inflammatory cytokines.

Human IL-1 epsilon was transfected into COS-1 cells. Several days after the transfection, conditioned medium (containing the transiently expressed IL-1 epsilon) was harvested. Human foreskin fibroblast (HFF) cells were incubated for 18 hours at 37□C with this conditioned medium diluted 1:1 with fresh 0.5% serum-containing medium, or alternatively with conditioned medium from control COS-1 cells transfected with the empty expression vector, diluted 1:1 with fresh 0.5% serum-containing medium.

Following treatment with the conditioned medium from COS-1 cells, the HFF cells were washed twice with PBS and removed from the tissue culture vessel with versene (non-trypsin reagent). Cell-surface ICAM-1 levels were measured by staining with anti-CD54-PE antibody (Pharmingen, San Diego, Calif.) on ice for one hour followed by washing and FACS-based detection.

HFF cells incubated in conditioned medium from control COS-1 cells exhibited a slight increase in ICAM-1 levels, relative to untreated cells. On the other hand, HFF cells that were treated with conditioned medium from COS-1 cells that had been transfected with epsilon exhibited a two-fold increase in cell-surface ICAM-1 levels. The level of ICAM-1 staining seen on the IL-1 epsilon treated HFF cells was comparable to that induced on the same cells by purified IL-1 beta.

EXAMPLE VI

Modulation of Cytokine Levels in Dendritic Cells by IL-1 Epsilon

The following describes tests that were carried out to determine whether IL-1 epsilon is capable of modulating cytokine secretion in dendritic cells.

Monocyte-derived dendritic cells (MoDC) are obtained essentially as described by Pickl et al. (J. Immunol. 157: 3850,1996). Briefly, highly purified CD14(bright) peripheral blood monocytic cells are obtained from peripheral blood using an AutoMACS cell sorting system and anti-CD 14 magnetic microbeads (Miltenyi Biotec, Bergisch Gladbach, Germany). The monocytic cells are cultured in the presence of IL-4 and GM-CSF for seven days to yield MoDC.

MoDC are treated for two to three days in the presence or absence of IL-1 epsilon at varying concentrations; lipopolysaccharide (LPS) at 1Ong/ml is used as a positive control, and heat-inactivated IL-1 epsilon (heated at 100 degrees C. for 30 minutes) is used as a negative control. Cells are separated from the supernatant medium by centrifugation.

The supernatant medium is analyzed for soluble cytokine levels using a suitable assay (for example, the Luminex® multi-plex cytokine assay; Luminex Corporation, Austin, Tex.). Following two day culture, the supernatant was harvested and assayed for several cytokines including IL-10, IL-2, IL4, IL-6, IL-8, IL-12 (p70 heterodimer), TNF-alpha, IFN-gamma, and GM-CSF.

The results of this assay indicated that IL-1 epsilon induced MoDC to secrete significant levels of IL-10; secretion of IL-10 was confirmed by ELISA substantially as described below. The results indicated that IL-1 epsilon-treated cells produced over 8 times more IL-10 as compared to cells treated with media only. This activity was observed in two separate experiments and was eliminated by heat denaturation (indicating that the increase in IL-10 was attributable to a heat-labile molecule, and not heat-stable LPS).

For analysis of the induction of cytokine mRNA, the cells are harvested and total RNA is isolated (for example, using an RNeasy® Total RNA System mini-kit, QIAGEN, Venlo, The Netherlands) and analyzed in a suitable, real-time quantitative polymerase chain reaction (PCR) analysis. Quantitative RT-PCR was performed using the ABI PRISM® 7700 Sequence Detection System (Applied Biosystems, Foster City, Calif.) and TaqMan® reagents (Applied Biosystems). This analysis indicated that IL-1 epsilon strongly induced mRNA levels of IL-1 alpha and IL-1 beta (approximately 10-15 fold above control). There was also a strong induction of the p40 subunit of IL-12 but not the p35 subunit. A modest increase in IL-10 and slight increases in Toll-like Receptors (TLR; Rock et al., *Proc. Natl. Acad. Sci. USA* 95:588, 1998; Hemmi et al., *Nature* 408:740, 2000) 4, 5, and 9, and B7-DC (Tseng et al., *J. Exp. Med.* 193:839, 2001) was also observed. In all cases, heat inactivation of IL-1 epsilon abolished the observed gene induction.

EXAMPLE VII

Effect of IL-1 Epsilon on Mixed Lymphocyte Reaction (MLR)

The following describes tests carried out to determine the effects of IL-1 epsilon on TNF-alpha, IFN-gamma, and IL-10 secretion in a mixed leukocyte reaction (MLR) assay.

Briefly, MoDCs are generated as described above. Purified CD3+ allogeneic T cells are obtained from freshly drawn blood using an AutoMACS cell sorting and anti-CD3 magnetic microbeads system (Miltenyi Biotec).

The allogeneic T cells are then mixed with MoDCs at a 1:10 MoDC:T ratio in quadruplicate in the presence of IL-1 epsilon at varying concentrations from 5 ng.ml to 200 ng/ml, or control preparations. The ensuing mixed lymphocyte reaction (MLR) is allowed to proceed for four days, and supernatants are harvested and assayed for TNF-alpha, IFN-gamma, and IL-10 using a suitable assay as described previously (for example, the Luminex® multi-plex cytokine assay, DELFIA® or ELISA substantially as described below).

Using a DELFIA® to detect cytokines, it was found that IL-10 levels were increased above control using a dose of 5 ng/ml IL-1 epsilon (untagged, produced in *E. coli*) and were further increased by addition of IL-1 epsilon up to 200 ng/ml. At doses of 25 ng/mi and higher, IL-1 epsilon caused increased TNF-alpha and interferon-gamma levels as well.

This activity was observed in two separate experiments and was eliminated by heat denaturation of the protein prep, indicating that endotoxin contamination is not the cause. The positive control was a mixture of 40 micrograms/ml SAC (heat killed *Staphlyococcus aureus* cells (Pansorbin), Calbiochem; La Jolla, Calif.) and 1 microgram/ml CD40L (Immnunex Corporation, Seattle, Wash.), and the negative control was media; a heat inactivated sample of IL-1 epsilon at 25 ng/ml was also included as a control for endotoxin contamination. A Flag®-polyHis version of this protein did not read out in this assay when used at 25 ng/ml.

EXAMPLE VIII

Cytokine ELISA

The following describes an Enzyme-Linked Immunosorbent Assay (ELISA) that is useful to detect and/or quantitate secreted proteins. The Example describes an assay specific for IL-10; those of skill in the art will recognize that a similar assay cold be used to detect other molecules.

ELISA plates (for example, Costar® EIA/RIA 96 well easy wash plates, Corning Incorporated Life Sciences, Acton, Mass.) were coated overnight with 100 microliter of a 2 micrograms/ml mixture of Rat-anti-huIL-10 capture antibody (BD Pharmingen, San Diego, Calif.) in binding solution (0.1M $NaH_2PO_4$, pH 9.0) at 4 degrees C. Plates were washed with wash buffer (phosphate buffered saline, or PBS, 0.5% Tween 20) four times (400 microliters/well/wash), then one time with PBS without Tween. Plates were blocked with 100 microliters of 5% non-fat dry milk in PBS for 1 hour at room temperature (RT), and then washed with wash buffer six times.

Samples and controls were added to separate wells (100 microliters/well); serial dilutions of a standard protein, recombinant HuIL-10 (BD Pharmingen) in PBS+3% BSA (starting at 10 ng/ml in 3-fold dilutions through 7 points as a standard curve, with an eighth point as a blank) was used to generate a standard curve for quantitation. The plates were incubated for one hour at RT, then washed with wash buffer six times as previously described, and incubated with biotinylated-rat-anti-HuIL-10 (BD Pharmingen; 100 microliters/well of a 200 ng/ml mixture in PBS+3% BSA) for one hour at RT. The plates were then washed six times with wash buffer as before, and streptavidin-conjugated horse radish peroxidase (SA-HRP; Zymed Laboratories, Inc., South San Francisco, Calif.; 100 microliters/well of a 1:4000 dilution in PBS+3% BSA) was added.

After incubating at RT for 30 minutes, the plates were washed for the final time as described above, and color was developed by adding 100 microliters/well of Tetramethyl-benzidene (TMB) substrate (a 1:1 mixture of TMB Peroxidase Substrate: Peroxidase Solution, Kirkegaard & Perry Laboratories, Inc., Gaithersburg, Md.). The plates were incubated for 30 minutes at RT, at which time color development was stopped with 100 microliters/well of 2N $H_2SO_4$. The plates were read at 450 nm wavelength on a Molecular Dynamics (Molecular Dynamics, Sunnyvale, Calif.) plate reader, a standard curve was prepared, and the quantity of IL-10 in the samples determined by comparison to the standard curve.

EXAMPLE IX

Cytokine DELFIA

The following describes a DELFIA® (dissociated enhanced lanthanide fluoroimmunoassay; PerkinElmer Life-Sciences, Wallac Oy., Turku, Finland) that is useful to detect and/or quantitate secreted proteins. The Example describes an assay specific for IL-10; those of skill in the art will recognize that a similar assay could be used to detect other molecules.

Briefly, DELFIA® plates (i.e., Costar® high binding 96-well plates, Corning Incorporated Life Sciences, Acton, Mass.) are coated with a detection (or capture) antibody (preferably a monoclonal antibody; 50 microliters of antibody solution containing 2 micrograms antibody/mi in PBS) at 4 degrees C. for 24 hours. Plates are washed with wash buffer (phosphate buffered saline, or PBS, 0.05% Tween 20) four times (300 microliters/well/wash), then used in an assay or stored.

Fifty microliters each of test supernatants and cell specific controls are added to separate wells of an antibody-coated plate; dilutions of standard proteins are used to generate a standard curve for quantitation. Test supernatants and controls are incubated in the antibody coated plate to allow binding of cytokine to the antibody. Plates are then washed and a polyclonal biotinylated detection antibody is added at a concentration of 10 nM in 50 microliters and incubated to allow binding to the captured cytokine. Plates are washed and Streptavidin-Europium (Eu) is added to the plate at a final concentration of 1 nM (0.06 micrograms/mil) in 50 microliters and incubated to allow binding to the biotinylated detection antibody. Plates are again washed and 100 microliters of enhancement solution is added to bind the Eu. The Eu in solution is then detected by time resolved fluorescence and the amount of cytokine secreted can be quantitated relative to standards which are added to each plate.

DELFIA® is amenable to full or partial automation (for example, using a Sagian Bioassay core system, Beckman Coulter, Inc., Fullerton, Calif., in combination with a plate reader such as a VICTOR2™, PerkinElmer LifeSciences), thereby rendering it useful for high-throughput testing.

EXAMPLE X

Preparation of Antibodies to Human IL-1 Epsilon

Polyclonal antibodies are readily generated from a variety of sources, for example, horses, cows, goats, sheep, dogs, chickens, rabbits, mice, or rats, using procedures that are well-known in the art. In general, purified polypeptides of the invention, or a peptide based on the amino acid sequence of polypeptides of the invention that is appropriately conjugated, is administered to the host animal typically through parenteral injection. The immunogenicity of these polypeptides can be enhanced through the use of an adjuvant, for example, Freund's complete or incomplete adjuvant. Following booster immunizations, small samples of serum are collected and tested for reactivity to the polypeptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530.

Monoclonal antibodies are readily prepared using well-known procedures, see for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, host animals, such as Balb/c mice, are injected intraperitoneally at least once, and preferably at least twice at about 3 week intervals with isolated and purified polypeptides or conjugated polypeptides of the invention, optionally in the presence of adjuvant. Preferably, at least about 10 µg of isolated and purified polypeptide of the invention or peptides based on the amino acid sequence of polypeptides of the invention in the presence of RIBI adjuvant (RIBI Corp., Hamilton, Mont.) is used. Mouse sera are then assayed by conventional dot blot technique or antibody capture (ABC) to determine which animal produces the highest level of antibody and whose spleen cells are the best candidate for fusion.

Approximately two to three weeks later, the mice are given an intravenous boost of the polypeptides or conjugated polypeptides (such as 3 µg suspended in sterile PBS). Mice are later sacrificed and spleen cells fused with commercially available myeloma cells, such as Ag8.653 (ATCC CRL-1580), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG) or more preferably, 50% PEG: 10% DMSO (Sigma). The fusion is plated out into, for example, 96-well flat bottom plates (Corning) containing an appropriate medium, such as HAT supplemented DMEM media, and allowed to grow for about eight days. Supernatants from resultant hybridomas are collected and added to, for example, a 96-well plate for 60 minutes that is first coated with goat anti-mouse Ig. Following washes, $^{125}$I-polypeptide or peptides of the invention are added to each well, incubated for 60 minutes at room temperature, and washed four times. Positive wells can be subsequently detected by conventional methods, such as autoradiography at −70 degrees C. using Kodak X-Omat S film. Other suitable means of identifying antibodies that bind IL-1 epsilon may be used (including, for example, ELISA, IFA, or one of the aforementioned assays using cells that respond to IL-1 epsilon).

Positive hybridoma cells can be injected intraperitoneally into syngeneic rodents to produce ascites containing high concentrations (for example, greater than 1 milligram per milliliter) of anti-IL-1 epsilon polypeptides monoclonal antibodies. Alternatively, positive hybridoma cells can be grown in bulk culture. Monoclonal antibodies are subsequently purified, such as over a Protein A or G column (Pharmacia, Uppsala, Sweden) or by affinity chromatography.

Antibodies can be further tested to evaluate their effects on the ability of IL-1 epsilon to induce a biological activity (for example, induction of inflammatory cytokines in MoDC, induction of ICAM-1 on HFF cells, phosphorylation of IKBalpha, p38 MAP kinase, and/or Stress-Activated Protein Kinase (SAPK/JNK), or other markers of IL-1 epsilon biological activity). An antibody that increases the ability of IL-1 epsilon to induce a biological activity is referred to as an agonistic antibody, whereas an antibody that decreases the ability of IL-1 epsilon to induce a biological activity is referred to as an antagonistic antibody. Both types of antibodies may be generated and identified by means that are well known in the art, and will have uses in detection or purification of IL-1 epsilon, as reagents for research or clinical use, and in therapy and/or diagnosis of conditions mediated by IL-1 epsilon, as described herein.

EXAMPLE XI

Mouse Inflammatory Bowel Disease Models

This example describes several mouse models of inflammatory bowel disease (IBD), which includes Crohn's Disease and ulcerative colitis. Inflammatory bowel disease in animals can either occur spontaneously or can be experimentally induced. It is necessary to exercise care when selecting IBD models to study to ensure that the particular model selected appropriately represents the relevant stage of the inflammatory process under investigation. Particularly useful models of IBD include:

A. Oral Administration of Dextran Sulfate Sodium (DSS)

The DSS induction model can be used to induce either chronic or acute IBD. In the acute protocol, mice are given DSS (preferably with a molecular weight of 40 Kd; from 2% to 8%) in their drinking water for from one to eight days. The percent DSS and the duration of induction will vary depending on the strain of mouse used (for example, C3H/HeJ, C3H/HeJBir, NOD and NOD/SCID mice are highly susceptible, DBA/2, C57BL/6, BALB/c and 129/SvJ mice are moderately susceptible, with varying degrees of susceptibility relative to each other, FVB mice are moderately resistant, and NON/Ltj mice are resistant to DSS induced colitis). In the acute model, DSS is withdrawn after the induction phase. To induce chronic colitis, 2-8% DSS is administered for from 5 to seven days followed by administration of water for ten days; this cycle is repeated three to four times.

DSS-induced colitis is marked by profound inflammation in the colon of animals characterized by crypt destruction, mucosal ulceration, erosions and infiltration of lymphocytes and neutrophils into the mucosal tissue. Histopathologic changes are individually scored as 0 (no findings), 1 (minimal), 2 (mild), 3 (moderate), 4 (severe) for each of the following parameters: increased lymphocytes, increased neutrophils, ulceration, edema, crypt degeneration, and crypt regeneration. Total lesion score, crypt length and number of ulcers are also determined and used to gage severity of colitis.

B. Anti-CD3-Induced Ileitis

Mice (for example, BALB/c, C57BL/6 or MPJ mice, 6-16 weeks of age) are given a single intraperitoneal (i.p.) injection of anti-CD3epsilon antibody or control Ab (50 micrograms diluted in 500 microliters PBS, pH 7.4). In wildtype mice such as those listed above, this treatment reliably induces diarrhea without being lethal. Immunosuppressants such as cyclosporin A (CsA, 50 mg/kg) or dexamethasone (Dex, 50 mg/kg) may be given i.p. either as a single dose at the same time as anti-CD3 antibody, or daily for a total of three injections beginning at the time of anti-CD3 injection, as control molecules that downregulate any ensuing immune response and prevent or ameliorate anti-CD3-induced ileitis.

Mice are monitored for clinical signs of ileitis; mice may be sacrificed at varying time points for histopathologic analysis and/or testing by other means to evaluate apoptosis in gut tissue. For histopathology, hematoxylin and eosin (H&E) stained tissue sections of paraffin embedded intestinal specimens are graded in a blinded fashion, for example by using a quantitative histology score based on the frequency of apoptotic epithelial cells within the epithelium and the ratio of villus height to crypt length. Histological alterations of the small intestinal mucosa that may be observed include a reduced villus height, increased thickness of the crypt region, loss of Paneth cells, goblet cells and IEL in the epithelial layer and severe morphologic changes of the epithelial cells. In the villi, the enterocytes may have lost their columnar and polarized morphology and become flattened. In the crypt region, numerous apoptotic bodies may identified in the epithelium.

C. MdrKO Spontaneous Colitis

The MDR gene family was identified by an ability to confer multiple drug resistance in cell lines. Three genes have been identified in rodents (mdr1, mdr2 and mdr3), and two in humans (MDR1, MDR3). The mouse mdr1a gene encodes a 17 OkDa transmembrane protein that is expressed in many tissues, including intestinal epithelial cells and subsets of lymphoid and hematopoietic cells. Its function in these cells is currently unknown, however, mice deficient in mdr1a spontaneously develop colitis. In humans, MDR1 may be associated with IBD susceptibility (Satsangi et al., *Nat. Genet.* 14:199, 1996; Brant et al., *Gastroenterology*, 118:A331, 2000), while decreased MDR1 expression has been reported in mucosal tissue from both CD and UC patients (Lawrance et al., *Hum. Mol. Genet.* 10: 445, 2001; Farrell et al., *Gastroenterology*, 118:279, 2000). Mdr1 a knockout mice (MdrKO) provide a model of both acute (spontaneous) and chronic (DSS-induced) IBD, similar to that seen in humans, where IBD is generally a mixture of both chronic and acute inflammation. Acute colitis in MdrKO mice is marked by the spontaneous appearance of diarrhea and bloody stools in a subset of the mice; chronic colitis is induced by administering 3% w/v DSS for seven days in drinking water, followed by normal water.

Histopathologic changes are individually scored as 0 (no findings), 1 (minimal), 2 (mild), 3 (moderate), 4 (severe) for each of the following parameters: increased mononuclear cells, increased neutrophils, ulceration, edema, crypt degeneration, and hyperplasia.

D. Helicobacter-Induced Colitis

Various strains of mice with immunologic defects (i.e., IL-10$^{-/-}$ mice, recombinase-activating gene (Rag)1$^{-/-}$ mice, T-cell receptor alpha (TCRalpha)$^{-/-}$ mice) are susceptible to colitis induced by infection with *Helicobacter* spp., as described in Burich et al. (*Am J. Physiol Gastrointest Liver Physiol* 281:G764, 2001). Moreover, luminal bacteria appear to be an important factor contributing to the development of IBD in mice and humans. Accordingly, introduction of *Helicobacter* spp. into immunodeficient mice also serves as an animal model of IBD humans (Burich et al. supra). In MdrKO mice, different species of *Helicobacter* may have different effects on spontaneous colitis; *H. bilis* infection induces IBD at a much earlier age, and the phenotypic appearance of *Helicobacter*-induced disease is similar, but not identical, to spontaneous IBD. In contrast, there is minimal disease in *H. hepaticus*-infected mdr1a-/- mice, and *H. hepaticus* appears to delay onset of spontaneous IBD. Accordingly, those of skill in the art can utilize a *Helicobacter*-based model of IBD substantially as described by Burich et al. supra.

EXAMPLE XII

Mouse Asthma Models

This example describes a mouse model of asthma. Mice (for example, BALB/c) are sensitized with antigen (for example, ovalbumin [OVA]) by intraperitoneal injection of the antigen in alum. Several sensitization schemes are known in the art; a preferred scheme is to inject 10 micrograms of OVA three times at one week intervals (i.e., on day −21, day −14 and day −7). The mice are then challenged with antigen either by aerosol exposure (5% OVA) or intranasal administration (0.1 mg OVA). The challenge schedule may be selected from among shorter terms (i.e., daily challenge on days 1, 2 and 3) or longer terms (i.e., weekly challenge for two to three weeks). The endpoints that are measured can include airway hyperreactivity, bronchoalveolar lavage (BAL) cell number and composition, in vitro draining lung lymph node cytokine levels, serum IgE levels, and histopathologic evaluation of lung tissue. Other animal models of asthma are known, and include the use of other animals (for example, C57BL/6 mice), sensitization schemes (for example, intranasal inoculation, use of other adjuvants or no adjuvants, etc.) and/or antigens (including peptides such as those derived from OVA or other proteinaceous antigens, ragweed extracts or other extracts such as those used in desensitization regimens, etc.).

EXAMPLE XIII

Mouse Collagen Induced Arthritis Model

This example describes two mouse models of rheumatoid arthritis, both of which are induced by immunization with collagen (eg., collagen-induced arthritis or CIA). One model is dependant on tumor necrosis factor (TNF), the other is TNF-independent. Those of skill in the art recognize that other animals models of rheumatoid arthritis exist, and further that various parameters within the models can be adjusted (see, for example, Luross and Williams, *Immunology* 103:407, 2001; Schaller et al., *Nat Immunol* 2:74, 2001; Bober et al., *Arthritis Rheum* 43:2660, 2000; or Weyand, C. M. in *Rheumatology* (Oxford) 2000 June, pgs: 3-8)).

TNF-dependent CIA is induced in male, wild-type (wt) DBA/1 mice substantially as a modification of the protocol described by Courtenay,. J. S. et al. (*Nature* 283:666, 1980) by immunization of mice with Type II collagen (CII; 100-200 micrograms) in complete Freund's adjuvant (CFA), followed by a booster of CII (200 micrograms) in incomplete Freund's adjuvant (IFA) approximately three weeks later. In untreated mice, CIA manifests in the paws, with increasing severity over time.

TNF-independent CIA is induced in male TNF Receptor double knockout (TNFR DKO) mice substantially as described above. TNFR DKO mice are mice that lack functional TNF receptors (both p55 and p75), and are described in Peschon, et al. (*J. Immunol.* 160:943, 1998).

Briefly, mice lacking functional p55 and p75 genes were generated in C57BLU6 background by gene targeting in embryonic stem cells. The TNFR DKO C57BL/6 mice were back-crossed on to the DBA/1 genetic background to yield mice that were homozygous for H-2q and were susceptible to development of CIA.

The severity of disease is judged by swelling and joint function of each paw, using a score from 0 to 4 (0=normal, no swelling; 1=swelling in 1 to 3 digits; 2=mild swelling in ankles, forepaw than three digits; 3=moderate swelling in multiple joints; 4=severe swelling with loss of function). The score for each paw is totaled for a cumulative score for each mouse; cumulative scores are totaled for the mice in each experimental group to yield a mean clinical score.

EXAMPLE XIV

Mouse Experimental Allergic Encephalomyelitis Model

This example describes two mouse models of demyelinating conditions; experimental autoimmune encephalomyelitis (or EAE) is designed to duplicate the secondary, immune mediated demyelination that occurs in multiple sclerosis.

A. Myelin Oligodendrocyte Glycoprotein (MOG)-Induced EAE in C57BL/6 Mice

EAE is induced in female C57BL/6 mice substantially as described by Mendel et al. (*Eur. J. Immunol.* 25:1951-59, 1995) by immunization of mice with an antigen derived from rat myelin oligodendrocyte glycoprotein (preferably the MOG35-55 peptide described by Mendel et al., supra). Other encephalitogenic antigens may be used, including, for example, whole spinal chord homogenate, purified whole myelin, myelin basic protein, proteolipid protein, myelin associated glycoprotein, myelin-associated oligodendrocyte basic protein, or encephalitogenic peptides derived from these antigens. The disease induction protocol of Mendel et al. may be modified to include the use of a lower dose of MOG35-55 for immunization (see below), no booster immunization, and the use of RIBI® adjuvant (Corixa Corporation, Seattle Wash.) instead of complete Freund's adjuvant.

To induce EAE, groups of age and weight-matched mice are given a dose of 100 micrograms of rat MOG35-55 emulsified in 0.2 ml RIBI® adjuvant and injected subcutaneously (for example, at three sites distributed over the shaved flank of a mouse). To induce EAE with accelerated onset, mice may be given an intravenous injection 500 ng pertussis toxin (List Biological Laboratory Inc, Campbell, Calif.), administered 48 hours after administration of MOG35-55.

B. Proteolipid Protein (PLP)-Induced EAE in SJL Mice

The PLP/SJL model results in a relapsing-remitting course of disease that mimics the course often seen in MS; however, SJL mice are susceptible to anaphylaxis, and care must be given in choosing and administering therapeutic agents to avoid induction of an anaphylactic response. EAE is induced in female SJL mice substantially as described by McRae et al. et al. (*J. Neuroimmunol.* 38:229, 1992) by immunization of mice with an antigen derived from rat proteolipid protein (preferably the PLP13-151(S) peptide described by McRae et al., supra). Other encephalitogenic antigens may be used, including, for example, whole spinal chord homogenate, purified whole myelin, myelin basic protein, proteolipid protein, myelin associated glycoprotein myelin-associated oligodendrocyte basic protein, or encephalitogenic peptides derived from these antigens. The disease induction protocol of McRae et al. may be modified as described above. EAE is reliably induced in SJL/J mice actively immunized with PLP 13-151(S) or another, suitable PLP-related antigen. Alternatively, EAE can be induced by adoptive transfer of PLP-specific T cells.

Administration of FIL1 antagonist(s) or control for either or both models is initiated on the day after administration of the encephalitogenic peptide (day 1) and continued through day 11. Varying injection schedules can be used to evaluate the efficacy of the FIL1 antagonist(s). Each mouse is injected intraperitoneally every other day (or according to the selected injection schedule) with 0.2 ml pyrogen-free phosphate-buffered saline (PBS) or 0.2 ml PBS containing FIL1 antagonist(s) or control. Endotoxin levels are monitored and must be less that <10 EU/mg of protein for all reagents. Mice are monitored daily for 30 to 35 days for weight loss, disease onset and severity of clinical signs of EAE by an independent observer blinded to the treatment groups.

The severity of EAE is assessed using either a standard EAE index system in which "0" is used to indicate an asymptomatic mouse and clinical scores ranging from 0.5 to 4 are used to indicate varying degrees of ascending paralysis, or a slightly modified version of the commonly used EAE scoring system. In the latter system, "0" indicates a mouse with no evidence of disease and scores of 1-5 indicate varying degrees of ascending paralysis as follows: 1, tail paralysis; 2, hind limb weakness; 3, partial hind limb paralysis; 4, complete hind limb paralysis; 5, moribund or dead. The disease protocol described above induces an acute episode of disease in control mice (peak score of 2-4) from which most recover at least partially. Thus the acute episode of disease is not lethal and mice do not reach a score of 5. The aforedescribed scale may be modified to include a score of "0.5" which is given to mice that show the earliest signs of EAE but that do not exhibit complete paralysis of the tail. Mice given a score of 0.5 exhibit some or all of the following symptoms: overnight weight loss of 1-2 grams; noticeable tremor when held up by the tail; and weakness at the distal tip of the tail.

The median day of onset of EAE is determined by Kaplan-Meier Survival analysis. Significant differences in onset between groups are assessed using a Log-Rank comparison. Fischer's exact test is used to analyze the statistical significance of differences in the incidence of EAE among the groups of mice.

EXAMPLE XV

Mouse Cuprizone-Induced Demyelinating Disease Model

This example describes a mouse model (cuprizone-induced demyelinating disease or CIDD) that is designed to mimic a type of demyelination that occurs in some cases of multiple sclerosis referred to as primary demyelination. CIDD is induced by feeding cuprizone (bis-cyclohexanone-oxaldihydrazone, a copper chelator) to mice substantially as described by Matsushima et al. (*Brain Pathol.* 11:107, 2001). At low doses of cuprizone, mature oligodendrocytes in the CNS are specifically insulted and they become unable to provide support for myelin. Demyelination occurs when the damaged myelin is stripped from the axons by microglia.

Some advantages of the CIDD model are that it reproducibly results in massive demyelination in a large area of the mouse brain and it is reversible if cuprizone is removed from the diet. The model appears well suited for profiling gene expression during various stages of demyelination and remyelination. The model has been established in C57BL/6 mice, so it is also suitable for use in KO (knockout) or Tg (transgenic) mice with the B6 background. However, there are no obvious clinical signs associated with the demyelinating process, so analysis must be done by histology.

The specification is most thoroughly understood in light of the teachings of the references cited within the specification, which are hereby incorporated by reference. The embodiments within the specification provide an illustration of embodiments of the invention and should not be construed to limit the scope of the invention. The skilled artisan recognizes many other embodiments are encompassed by the claimed invention.

What is claimed is:

1. A method of treating an individual afflicted with an inflammatory and/or autoimmune disease selected from the group consisting of: asthma, inflammatory bowel disease, psoriasis, and combinations thereof, comprising administering to the individual an antagonistic antibody immunoreactive with IL-1 epsilon comprising the amino acid sequence set forth in SEQ ID NO:8 or 13, wherein the antibody decreases induction of a biological activity of the IL-1 epsilon selected from the group consisting of: expression of one or more cytokines selected from the group consisting of IL-1 alpha, IL-1 beta, TNF-alpha, IL-10, IFN-gamma, IL-12 p40, IL-6; expression of one or more cell-surface molecules selected from the group consisting of ICAM-1, TLR4, TLR5, TLR9, DC-B7; and activation of one or more signaling molecules selected from the group consisting of NFkappaB, p38 MAP kinase, Stress-Activated Protein Kinase (SAPK/JNK).

2. The method of claim 1, wherein inflammatory and/or autoimmune disease is selected from the group consisting of: Crohn's Disease, ulcerative colitis, psoriatic arthritis, psoriasis, asthma, and combinations thereof.

3. The method of claim 2, wherein the antibody is a monoclonal antibody.

4. The method of claim 3, wherein the monoclonal antibody is selected from the group consisting of chimeric antibody, a humanized antibody, a human antibody, and an antigen-binding fragment of the aforementioned antibodies.

5. The method of claim 1, wherein the antibody is a monoclonal antibody.

6. The method of claim 5, wherein the monoclonal antibody is selected from the group consisting of a chimeric antibody, a humanized antibody, a human antibody, and an antigen-binding fragment of the aforementioned antibodies.

* * * * *

UNITED STATES PATENT AND TRADEMARK OFFICE
CERTIFICATE OF CORRECTION

PATENT NO. : 7,261,894 B2
APPLICATION NO. : 10/991812
DATED : August 28, 2007
INVENTOR(S) : Sims et al.

Page 1 of 1

It is certified that error appears in the above-identified patent and that said Letters Patent is hereby corrected as shown below:

Column 52 , Line 19: change "wherein inflammatory" to -- wherein the inflammatory --

Column 52, Line 26: change "of chimeric" to -- of a chimeric --

Column 52, Line 27: change "antibody,a human" to -- antibody, a human --

Signed and Sealed this

Thirty-first Day of March, 2009

JOHN DOLL
*Acting Director of the United States Patent and Trademark Office*